(12) United States Patent
Harmon et al.

(10) Patent No.: US 12,098,200 B1
(45) Date of Patent: Sep. 24, 2024

(54) BRAIN-TARGETING SINGLE DOMAIN ANTIBODIES AND PURIFICATION METHODS

(71) Applicant: National Technology & Engineering Solutions of Sandia, LLC, Albuquerque, NM (US)

(72) Inventors: Brooke Nicole Harmon, Livermore, CA (US); Maxwell Stefan, Pleasanton, CA (US); Jennifer Schwedler, Livermore, CA (US); Christopher Sumner, Livermore, CA (US); Yooli Kim Light, Pleasanton, CA (US); Catherine Margaret Mageeney, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 17/964,213

(22) Filed: Oct. 12, 2022

(51) Int. Cl.
*C07K 16/28* (2006.01)
*A61P 31/14* (2006.01)
*C12N 15/63* (2006.01)

(52) U.S. Cl.
CPC ............. *C07K 16/28* (2013.01); *A61P 31/14* (2018.01); *C12N 15/63* (2013.01); *C07K 2317/565* (2013.01); *C07K 2317/569* (2013.01)

(58) Field of Classification Search
CPC ............. C07K 16/28; C07K 2317/565; C07K 2317/569; A61P 31/14; C12N 15/63
See application file for complete search history.

(56) References Cited

U.S. PATENT DOCUMENTS 12,024,551 B1 * 7/2024 Harmon ................ C07K 16/10
2019/0091150 A1   3/2019 Brinker et al.

OTHER PUBLICATIONS

Winkler et al. (2000). The Journal of Immunology 165(8): 4505-4514. (Year: 2000).*
Schroeder and Cavacini. (2010). Journal of Allergy and Clinical Immunology 125: S41-S52. (Year: 2010).*
Sela-Chang et al. (2013). Frontiers in Immunology 4: 302. (Year: 2013).*
Bannas et al. (2017). Frontiers in Immunology 8: 1603. (Year: 2017).*
Jovcevska and Muyldermans. (2020). BioDrugs 34: 11-26. (Year: 2020).*
Ruiz-Lopez and Schuhmacher. (2021). Biomolecules 11: 1131. (Year: 2021).*
Wilton, Emily E. et al., "sdAb-DB: The Single Domain Antibody Database," ACS Synth. Biol. (2018) 7:2480-2484.
Løset, Geir Age et al., "Expanding the Versatility of Phage Display II: Improved Affinity Selection of Folded Domains on Protein VII and IX of the Filamentous Phage"; PLos One (2011) 6(2):e 17433, 10 pages.
Stefan, Maxwell A. et al., "Development of potent and effective synthetic SARS-CoV-2 neutralizing nanobodies"; MABS (2021) 13(1):e1958663, 13 pages.
Roovers, Rob C. et al., "A bi-paratopic anti-EGFR nanobody efficiently inhibits solid tumour growth"; Int J Cancer. (2011) 129(8):2013-2024.
Gustafson, Heather H. et al., "Current state of in vivo panning technologies: designing specificity and affinity into the future of drug targeting"; Adv Drug Deliv Rev. (2018) 130:39-49. doi:10.1016/j.addr.2018.06.015.
McBride, Amber A. et al., "Pulmonary Delivery of Magnetically Targeted Nano-in-Microparticles"; Methods Mol Biol. (2017) 1530:369-378. doi: 10.1007/978-1-4939-6646-2_23.
Franks, Teri J. et al., "Resident Cellular Components of the Human Lung; Current Knowledge and Goals for Research on Cell Phenotyping and Function"; Proc Am Thorac Soc (2008) 5:763-766.
Freeman, Tami, "Transcranial ultrasound opens a pathway through the blood-brain barrier"; https://physicsworld.com/a/transcranial-ultrasound-opens-a-pathway-through-the-blood-brain-barrier/; Jun. 11, 2019, 3 pages.
Larsen, J. M. et al., "Recent Advances in Delivery Through the Blood-Brain Barrier," Current Topics in Medicinal Chemistry (2014) 14:1148-1160.
Zhang, L. et al., "SARS-CoV-2 crosses the blood-brain barrier accompanied with basement membrane disruption without tight junctions alteration," Sigal Transduction and Targeted Therapy (2021) 6:337, 12 pages, https://doi.org/10.1038/s41392-021-00719-9.

* cited by examiner

*Primary Examiner* — Julie Wu
*Assistant Examiner* — Elizabeth A Shupe
(74) *Attorney, Agent, or Firm* — Eschweiler & Potashnik, LLC; Samantha Updegraff

(57) ABSTRACT

Provided herein are single domain antibodies (sdAbs) configured for passing the blood brain barrier in a human or mammal brain. Methods of using such sdAbs are also described herein, such as methods of binding to brain cells, binding with and transporting other sdAbs with beneficial functionalities, binding to and transporting biochemical or pharmaceutical species with beneficial functionalities, and treating, diagnosing, or prophylactically treating a disease, malignancy, or condition.

19 Claims, 13 Drawing Sheets
Specification includes a Sequence Listing.

| SEQ ID NO. | CDR1 | SEQ ID NO. | CDR2 | SEQ ID NO. | CDR3 | Secondary Identifier |
|---|---|---|---|---|---|---|
| 1 | HYDGILD | 26 | DWSQDHTL | 51 | YRDLKQETT | sandia2-1 |
| 2 | QFFGHRT | 27 | SWSGGSKY | 52 | VRFNHSRGS | sandia2-2 |
| 3 | RYSDQYW | 28 | SASGRRTY | 53 | SWWRRRHKLDIR | sandia2-3 |
| 4 | QTFSQYT | 29 | RGQAGYTY | 54 | FPNHHRRDL | sandia2-4 |
| 5 | RTSGHYY | 30 | SASGRPTL | 55 | HYRYKGPRR | sandia2-5 |
| 6 | QTFSHYV | 31 | GTRSARKR | 56 | LWWGLGDARNKG | sandia2-6 |
| 7 | RTFGWRR | 32 | SSSDGFVY | 57 | DAQLPPEGP | sandia2-7 |
| 8 | SSYSGST | 33 | GTTDFDQY | 58 | TFNHSLASKLFNDIK | sandia2-8 |
| 9 | GAFGETR | 34 | AADSGTDT | 59 | GIKPDVGRY | sandia2-9 |
| 10 | RYASSWR | 35 | QGYQRFRT | 60 | VRTDNGEFA | sandia2-10 |
| 11 | RYASDYR | 36 | SWSGGSAR | 61 | SWHVEDLTLSEW | sandia2-11 |
| 12 | RYFSGQR | 37 | AGRDGRDY | 62 | RAYDDAIHQ | sandia2-12 |
| 13 | RAFGIYR | 38 | GGDAGHTR | 63 | YCDYNGVVPFFK | sandia2-13 |
| 14 | GTFQEQY | 39 | SSSDGTYY | 64 | ITRNYREPTPGR | sandia2-14 |
| 15 | TAYGWSR | 40 | RASAGYAQ | 65 | IGPHYDIRS | sandia2-15 |
| 16 | TFDQRSR | 41 | SWSDGSRK | 66 | AFFADAYTIPFY | sandia2-16 |
| 17 | RFDGELR | 42 | TWAGDSAR | 67 | SADLQNIWPGEHSKW | sandia2-17 |
| 18 | GSFSSTA | 43 | SRRGYSTY | 68 | HGKRSENIHTRAFYG | sandia2-18 |
| 19 | HSSGASR | 44 | SSSDGFVY | 69 | ARHFNDHYDDYANAW | sandia2-19 |
| 20 | RAFGIYR | 45 | GGDAGHTR | 70 | YWDYNGGVPFFK | sandia2-20 |
| 21 | STFSGDR | 46 | TQSQGTTA | 71 | GRSIVETDGHSIIRY | sandia2-21 |
| 22 | SAFDDVP | 47 | DWQGGWTD | 72 | RFNPINPHT | sandia2-22 |
| 23 | STFQGYR | 48 | SWRGGSQR | 73 | TIIHDQKDTPYY | sandia2-23 |
| 24 | TAFGQYR | 49 | SWSGGSAR | 74 | TWYYLEHLGEYR | sandia2-24 |
| 25 | GTFGQWR | 50 | GGDAGHTR | 75 | RRDLAGAQY | sandia2-25 |

*Fig. 3*

*Fig. 4*

| SEQ ID NO. | Full Nanobody: FR1-CDR1-FR2-CDR2-FR3-CDR3-FR4 | Secondary Identifier |
|---|---|---|
| 76 | EVQLQASGGGFVQPGGSLRLSCAASGHYDGILDMGWFRQAPGKEREFVSAISDWSQDHTLYADSVKGRFTISRDNSKNTVYLQMNSLRAEDTATYYCAYRDLKQETTYWGQGTQVTVSS | sandia2-1 |
| 77 | EVQLQASGGGFVQPGGSLRLSCAASGQFFGHRTMGWFRQAPGKEREFVSAISSWSGGSKYYADSVKGRFTISRDNSKNTVYLQMNSLRAEDTATYYCAVRFNHSRGSYWGQGTQVTVSS | sandia2-2 |
| 78 | EVQLQASGGGFVQPGGSLRLSCAASGRYSDQYWMGWFRQAPGKEREFVSAISSASGRRTYYADSVKGRFTISRDNSKNTVYLQMNSLRAEDTATYYCASWWRRRHKLDIRYWGQGTQVTVSS | sandia2-3 |
| 79 | EVQLQASGGGFVQPGGSLRLSCAASGQTFSQYTMGWFRQAPGKEREFVSAISRGQAGYTYYADSVKGRFTISRDNSKNTVYLQMNSLRAEDTATYYCAFPNHHRRDLYWGQGTQVTVSS | sandia2-4 |
| 80 | EVQLQASGGGFVQPGGSLRLSCAASGRTSGHYYMGWFRQAPGKEREFVSAISSASGRPTLYADSVKGRFTISRDNSKNTVYLQMNSLRAEDTATYYCAHYRYKGPRRYWGQGTQVTVSS | sandia2-5 |
| 81 | EVQLQASGGGFVQPGGSLRLSCAASGQTFSHYVMGWFRQAPGKEREFVSAISGTRSARKRYADSVKGRFTISRDNSKNTVYLQMNSLRAEDTATYYCALWWGLGDARNKGYWGQGTQVTVSS | sandia2-6 |
| 82 | EVQLQASGGGFVQPGGSLRLSCAASGRTFGWRRMGWFRQAPGKEREFVSAISSSDGFVYYADSVKGRFTISRDNSKNTVYLQMNSLRAEDTATYYCADAQLPPEGPYWGQGTQVTVSS | sandia2-7 |
| 83 | EVQLQASGGGFVQPGGSLRLSCAASGSSYSGSTMGWFRQAPGKEREFVSAISGTTDFDQYYADSVKGRFTISRDNSKNTVYLQMNSLRAEDTATYYCATFNHSLASKLFNDIKYWGQGTQVTVSS | sandia2-8 |
| 84 | EVQLQASGGGFVQPGGSLRLSCAASGGAFGETRMGWFRQAPGKEREFVSAISAADSGTDYADSVKGRFTISRDNSKNTVYLQMNSLRAEDTATYYCAGIKPDVGRYYWGQGTQVTVSS | sandia2-9 |
| 85 | EVQLQASGGGFVQPGGSLRLSCAASGRYASSWRMGWFRQAPGKEREFVSAISQGYQRFRTYADSVKGRFTISRDNSKNTVYLQMNSLRAEDTATYYCAVRTDNGEFAYWGQGTQVTVSS | sandia2-10 |
| 86 | EVQLQASGGGFVQPGGSLRLSCAASGRYASDYRMGWFRQAPGKEREFVSAISSWSGGSARYADSVKGRFTISRDNSKNTVYLQMNSLRAEDTATYYCASWHVEDLTLSEWYWGQGTQVTVSS | sandia2-11 |
| 87 | EVQLQASGGGFVQPGGSLRLSCAASGRYFSGQRMGWFRQAPGKEREFVSAISAGRDGRDYYADSVKGRFTISRDNSKNTVYLQMNSLRAEDTATYYCARAYDDAIHQYWGQGTQVTVSS | sandia2-12 |
| 88 | EVQLQASGGGFVQPGGSLRLSCAASGRAFGIYRMGWFRQAPGKEREFVSAISGGDAGHTRYADSVKGRFTISRDNSKNTVYLQMNSLRAEDTATYYCAYCDYNGVVPFFKYWGQGTQVTVSS | sandia2-13 |
| 89 | EVQLQASGGGFVQPGGSLRLSCAASGGTFQEQYMGWFRQAPGKEREFVSAISSSDGTYYADSVKGRFTISRDNSKNTVYLQMNSLRAEDTATYYCAITRNYREPTPGRYWGQGTQVTVSS | sandia2-14 |
| 90 | EVQLQASGGGFVQPGGSLRLSCAASGTAYGWSRMGWFRQAPGKEREFVSAISRASAGYAQYADSVKGRFTISRDNSKNTVYLQMNSLRAEDTATYYCAIGPHYDIRSYWGQGTQVTVSS | sandia2-15 |

*Fig. 5*

| 91 | EVQLQASGGGFVQPGGSLRLSCAASGTFDQRSRMGWFRQAPGKERE FVSAISSWSDGSRKYADSVKGRFTISRDNSKNTVYLQMNSLRAEDTAT YYCAAFFADAYTIPFYYWGQGTQVTVSS | sandia2-16 |
|---|---|---|
| 92 | EVQLQASGGGFVQPGGSLRLSCAASGRFDGELRMGWFRQAPGKERE FVSAISTWAGDSARYADSVKGRFTISRDNSKNTVYLQMNSLRAEDTAT YYCASADLQNIWPGEHSKWYWGQGTQVTVSS | sandia2-17 |
| 93 | EVQLQASGGGFVQPGGSLRLSCAASGGSFSSTAMGWFRQAPGKERE FVSAISSRRGYSTYYADSVKGRFTISRDNSKNTVYLQMNSLRAEDTAT YYCAHGKRSENIHTRAFYGYWGQGTQVTVSS | sandia2-18 |
| 94 | EVQLQASGGGFVQPGGSLRLSCAASGHSSGASRMGWFRQAPGKERE FVSAISSSSDGFVYYADSVKGRFTISRDNSKNTVYLQMNSLRAEDTAT YYCAARHFNDHYDDYANAWYWGQGTQVTVSS | sandia2-19 |
| 95 | EVQLQASGGGFVQPGGSLRLSCAASGRAFGIYRMGWFRQAPGKERE FVSAISGGDAGHTRYADSVKGRFTISRDNSKNTVYLQMNSLRAEDTAT YYCAYWDYNGGVPFFKYWGQGTQVTVSS | sandia2-20 |
| 96 | EVQLQASGGGFVQPGGSLRLSCAASGSTFSGDRMGWFRQAPGKERE FVSAISTQSQGTTAYADSVKGRFTISRDNSKNTVYLQMNSLRAEDTAT YYCAGRSIVETDGHSIIRYYWGQGTQVTVSS | sandia2-21 |
| 97 | EVQLQASGGGFVQPGGSLRLSCAASGSAFDDVPMGWFRQAPGKERE FVSAISDWQGGWTDYADSVKGRFTISRDNSKNTVYLQMNSLRAEDTAT YYCARFNPINPHTYWGQGTQVTVSS | sandia2-22 |
| 98 | EVQLQASGGGFVQPGGSLRLSCAASGSTFQGYRMGWFRQAPGKERE FVSAISSWRGGSQRYADSVKGRFTISRDNSKNTVYLQMNSLRAEDTAT YYCATIIHDQKDTPYYWGQGTQVTVSS | sandia2-23 |
| 99 | EVQLQASGGGFVQPGGSLRLSCAASGTAFGQYRMGWFRQAPGKERE FVSAISSWSGGSARYADSVKGRFTISRDNSKNTVYLQMNSLRAEDTAT YYCATWYYLEHLGEYRYWGQGTQVTVSS | sandia2-24 |
| 100 | EVQLQASGGGFVQPGGSLRLSCAASGGTFGQWRMGWFRQAPGKERE FVSAISGGDAGHTRYADSVKGRFTISRDNSKNTVYLQMNSLRAEDTAT YYCARRDLAGAQYYWGQGTQVTVSS | sandia2-25 |

*Fig. 6*

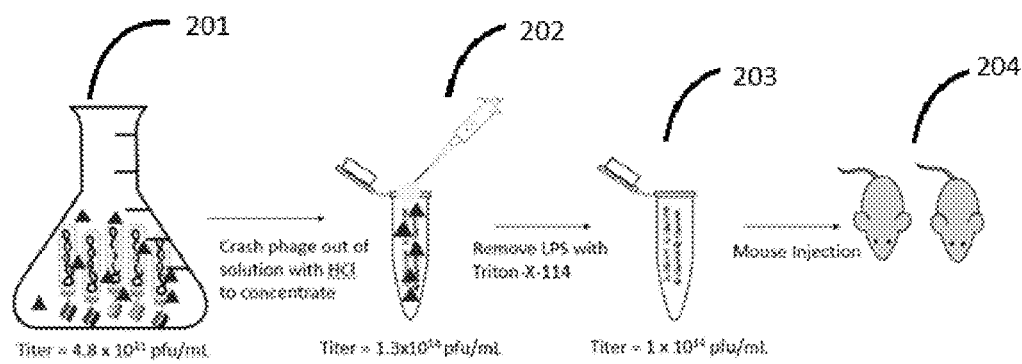
Fig. 8
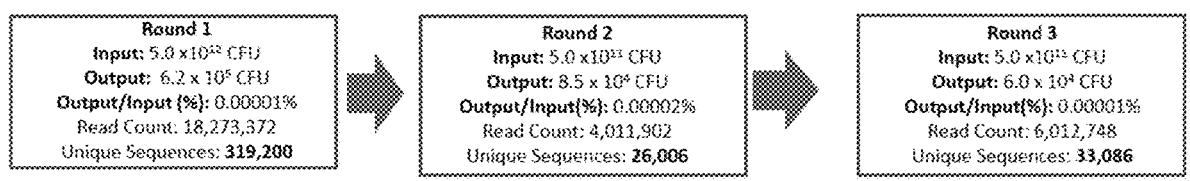
Fig. 9
Fig. 10

| SEQ ID NO: | Enrichment Factor | |
|---|---|---|
| | R2 | R3 |
| 76 | 0.5 | 469.4 |
| 77 | 0.5 | 453.1 |
| 78 | 0.5 | 397.3 |
| 79 | 0.7 | 393.2 |
| 80 | 1.2 | 157.5 |
| 81 | 1.7 | 126.4 |
| 82 | 3.0 | 116.7 |
| 83 | 4.5 | 94.6 |
| 84 | 2.7 | 89.3 |
| 85 | 30.2 | 81.8 |
| 86 | 2.5 | 78.2 |
| 87 | 4.2 | 69.5 |
| 88 | 7.2 | 62.5 |
| 89 | 5.7 | 61.8 |
| 90 | 6.7 | 61.4 |
| 91 | 6.2 | 61.0 |
| 92 | 9.5 | 59.9 |
| 93 | 4.2 | 52.0 |
| 94 | 4.0 | 51.6 |
| 95 | 13.0 | 50.8 |
| 96 | 9.7 | 48.6 |
| 97 | 5.7 | 47.8 |
| 98 | 4.2 | 46.0 |
| 99 | 5.7 | 44.9 |
| 100 | 9.0 | 43.8 |

*Fig. 11*

| SEQ ID NOs | |
|---|---|
| | FR1 |
| 405 | EVQLQASGGGFVQPGGSLRLSCAASG |
| | FR2 |
| 406 | MGWFRQAPGKEREFVSAIS |
| | FR3 |
| 407 | YADSVKGRFTISRDNSKNTVYLQMNSLRAEDTATYYCA |
| | FR4 |
| 408 | YWGQGTQVTVSS |

Fig. 14

EVQLQASGGGFVQPGGSLRLSCAASG-CDR1-MGWFRQAPGKEREFVSAIS-CDR2-
YADSVKGRFTISRDNSKNTVYLQMNSLRAEDTATYYCA-CDR3-YWGQGTQVTVSS       (SEQ ID NO:183)

EVQLQASGGGFVQPGGSLRLSCAASG-CDR1-MGWFRQAPGKEREFVSAIS-CDR2-
YADSVKGRFTISRDNSKNTVYLQMNSLRAEDTATYYCA-CDR3-YWGQGTQVTVSS       (SEQ ID NO:184)

EVQLQASGGGFVQAGGSLRLSCAASG-CDR1-MGWFRQAPGKEREFVAAIS-CDR2-
YYADSVKGRFTISRDNAKNTVYLQMNSLKPEDTATYYCA-CDR3-YWGQGTQVTVSS      (SEQ ID NO:185)

EVQLQASGGGFVQAGGSLRLSCAASG-CDR1-MGWFRQAPGKEREFVAAIS-CDR2-
YYADSVKGRFTISRDNAKNTVYLQMNSLKPEDTATYYCA-CDR3-YWGQGTQVTVSS      (SEQ ID NO:186)

| | |
|---|---|
| EVQLQASGGGFVQAGGSLRLSCAASG | (SEQ ID NO:190) |
| EVQLQASGGGFVQPGGSLRLSCAASG | (SEQ ID NO:191) |
| QVQLVESGGGSVQAGGSLRLSCTASGGSEY | (SEQ ID NO:192) |
| QVQLVESGGGSVQAGGSLRLSCTASG | (SEQ ID NO:193) |
| QVQLVESGGGSVQAGGSLRLSCTASGFSRE | (SEQ ID NO:194) |
| QVQLQESGPSLVRPSQTLSLTCTISGFSRE | (SEQ ID NO:195) |
| QVQLQESGPSLVRPSQTLSLTCTISG | (SEQ ID NO:196) |
| QVQLVESGGNLVQPGGSLRLSCAASGFTFG | (SEQ ID NO:197) |
| QVQLVESGGNLVQPGGSLRLSCAASG | (SEQ ID NO:198) |
| QVQLVESGGALVQPGGSLRLSCAASGFPVN | (SEQ ID NO:199) |
| QVQLVESGGALVQPGGSLRLSCAASGFTFG | (SEQ ID NO:200) |
| QVQLVESGGGLVQPGGSLRLSCAASGFTFG | (SEQ ID NO:201) |
| QVQLVESGGALVQPGGSLRLSCAASG | (SEQ ID NO:202) |
| QVQLVESGGGLVQAGGSLRLSCAASG | (SEQ ID NO:203) |
| QVQLVESGGGLMQAGGSLRLSCAVSG | (SEQ ID NO:204) |
| QVQLQESGGGLVQAGGSLRLSCAASG | (SEQ ID NO:205) |
| HVQLVESGGGLVQAGGSLRLSCAASG | (SEQ ID NO:206) |
| DVQLVESGGGLVQAGGSLRLSCAASG | (SEQ ID NO:207) |
| EVQLVESGGGLVQAGGSLRLSCAASG | (SEQ ID NO:208) |
| EVQLVESGGGVVQPGRSLRLSCAASGFTFD | (SEQ ID NO:209) |
| EVQLVESGGGVVQPGRSLRLSCAASG | (SEQ ID NO:210) |
| DVQLQASGGGLVQAGGSLRLSCAASGFKIT | (SEQ ID NO:211) |
| DVQLQASGGGLVQAGGSLRLSCAASG | (SEQ ID NO:212) |

| | |
|---|---|
| MGWFRQAPGKEREFVAAIS | (SEQ ID NO:220) |
| MGWFRQAPGKEREFVSAIS | (SEQ ID NO:221) |
| --WFRQAPGQEREAVA | (SEQ ID NO:222) |
| --WFRQAPGQEREAVAAIA | (SEQ ID NO:223) |
| --WVRQAPGKALEWLG | (SEQ ID NO:224) |
| --WVRQAPGKALEWLGRI | (SEQ ID NO:225) |
| --WFRQAPGQEREWLG | (SEQ ID NO:226) |
| --WFRQAPGQEREWLGRI | (SEQ ID NO:227) |
| --WVRQAPGGGLEWVA | (SEQ ID NO:228) |
| --WYRQATGKEREWVA | (SEQ ID NO:229) |
| MSWYRQATGKEREWVA | (SEQ ID NO:230) |
| MGWFRQAPGKEREFVAAIR | (SEQ ID NO:231) |
| MGWFRQAPGKEREFVAAI | (SEQ ID NO:232) |
| MGWFRQAPGKEREFVA | (SEQ ID NO:233) |
| MGWYRQAPGKERELVA | (SEQ ID NO:234) |
| MGWYRQAPGKERELVAA | (SEQ ID NO:235) |
| MGWYRQAPGKERELVAAID | (SEQ ID NO:236) |
| MGWYRQAPGKERELVAVIS | (SEQ ID NO:237) |
| MGWFRQAPGKEREGVA | (SEQ ID NO:238) |
| --WFRQAPGKEREGVA | (SEQ ID NO:239) |
| MGWFRQAPGKEREFVA | (SEQ ID NO:240) |
| --WFRQAPGKEREFVA | (SEQ ID NO:241) |
| --WVRQAPGKGPEWVA | (SEQ ID NO:242) |
| --WFRQAPGKEREFVS | (SEQ ID NO:243) |

| | |
|---|---|
| -YADSVKGRFTISRDNAKNTVYLQMNSLKPEDTATYYCA- | (SEQ ID NO:250) |
| YYADSVKGRFTISRDNAKNTVYLQMNSLKPEDTATYYCA- | (SEQ ID NO:251) |
| -YADSVKGRFTISRDNSKNTVYLQMNSLRAEDTATYYCA- | (SEQ ID NO:252) |
| YYADSVKGRFTISRDNSKNTVYLQMNSLRAEDTATYYCA- | (SEQ ID NO:253) |
| --------RFTISRDNAKNTVTLQMNNLKPEDTAIYYCA- | (SEQ ID NO:254) |
| --------RFTISRDNAKNTVTLQMNNLKPEDTAIYYCAA | (SEQ ID NO:255) |
| --------RLTITRDISKSQVSLSLSSVTLEDTAEYYCV- | (SEQ ID NO:256) |
| --------RLTITRDISKSQVSLSLSSVTLEDTAEYYCVY | (SEQ ID NO:257) |
| --------RFTISRDIAKNTVTLQMNNLKPEDTAIYYVY- | (SEQ ID NO:258) |
| --------RFTISRDIAKNTVTLQMNNLKPEDTAIYYVYA | (SEQ ID NO:259) |
| YYADSVKGRFTISRDNAKNTVTLQMNNLKPEDTAIYYCA- | (SEQ ID NO:260) |
| YYADSVKGRFTISRDNAKNTVTLQMNNLKPEDTAIYYCAA | (SEQ ID NO:261) |
| -YEDSVKGRFCISRDDARNTVYLQMNSLKPEDTAVYYCNV | (SEQ ID NO:262) |
| -YEDSVKGRFCISRDDARNTVYLQMNSLKPEDTAVYYCN- | (SEQ ID NO:263) |
| -YADSVKGRFTISRDNAKNSVYLQMNSLRVEDTAVYYCAR | (SEQ ID NO:264) |
| -YADSVKGRFTISRDNAKNSVYLQMNSLRVEDTAVYYCA- | (SEQ ID NO:265) |
| -YADSVKGRFTISRDNARNTVYLQMNSLKPEDTAVYYCAR | (SEQ ID NO:266) |
| -YADSVKGRFTISRDNARNTVYLQMNSLKPEDTAVYYCA- | (SEQ ID NO:267) |
| -YADSVKGRFTISRDNARNTVYLQMNSLKPEDTAVYYCAR | (SEQ ID NO:268) |
| --------RFTISRDNARNTVYLQMNSLKPEDTAVYYCAR | (SEQ ID NO:269) |
| -YADSVKGRFTISRDKGKNTVYLQMDSLKPEDTATYYCAA | (SEQ ID NO:270) |
| --------RFTISRDKGKNTVYLQMDSLKPEDTATYYCAA | (SEQ ID NO:271) |
| -YADSVKGRFTISRDKGKNTVYLQMDSLKPEDTATYYCA- | (SEQ ID NO:272) |
| --------RFTISRDKGKNTVYLQMDSLKPEDTATYYCA- | (SEQ ID NO:273) |
| YYADSVKGRFTISRDKAKNTVYLQMNSLKYEDTAVYYCA- | (SEQ ID NO:274) |
| -YADSVKGRFTISRDKAKNTVYLQMNSLKYEDTAVYYCA- | (SEQ ID NO:275) |
| YYADSVKGRFTISRDNAKNTVYLQMNSLKPEDTAVYYCA- | (SEQ ID NO:276) |
| LHNPALKSRLTITRDISKSQVSLSLSSVTLEDTAEYYCV- | (SEQ ID NO:277) |
| LHNPALKSRLTITRDISKSQVSLSLSSVTLEDTAEYYCVY | (SEQ ID NO:278) |
| LHNPALKSRFTISRDIAKNTVTLQMNNLKPEDTAIYYVYA | (SEQ ID NO:279) |
| -YADSVKGRFTISRDNAKNTVYLQMNSLKPEDTAVYYCAA | (SEQ ID NO:280) |
| -YADSVKGRFTISRDNAKNTVYLQMNSLKPEDTAVYYCA- | (SEQ ID NO:281) |
| YYADSVKGRFTISRDNAKNTVYLQMNSLKPEDTAVYYCAA | (SEQ ID NO:282) |
| --------RFTISRDNSKNTLYLQMNSLRAEDTAVYYCAR | (SEQ ID NO:283) |
| --------RFTISRDNAKNTVYLQMNSLKPEDTADYYCAA | (SEQ ID NO:284) |

| | |
|---|---|
| YWGQGTQVTVSS | (SEQ ID NO:290) |
| -WGQGTQVTVSS | (SEQ ID NO:291) |
| VWGPGLLLTVSS | (SEQ ID NO:292) |
| -WGPGLLLTVSS | (SEQ ID NO:293) |
| -WGQGTLVTVS- | (SEQ ID NO:294) |
| -WGQGTLVTVSS | (SEQ ID NO:295) |
| -WGQGTQVTVS- | (SEQ ID NO:296) |
| -WGQGTQVTVSS | (SEQ ID NO:297) |
| QWGQGTQVTVSS | (SEQ ID NO:298) |
| YWGQGTQVTVS- | (SEQ ID NO:299) |
| -WGQGTTVVVSS | (SEQ ID NO:300) |
| -WGKGTQVTVSS | (SEQ ID NO:301) |

*Fig. 16D*

SEQUENCE LISTING

```
Sequence total quantity: 409
SEQ ID NO: 1            moltype = AA   length = 7
FEATURE                 Location/Qualifiers
source                  1..7
                        mol_type = protein
                        organism = synthetic construct
SEQUENCE: 1
HYDGILD                                                                     7

SEQ ID NO: 2            moltype = AA   length = 7
FEATURE                 Location/Qualifiers
source                  1..7
                        mol_type = protein
                        organism = synthetic construct
SEQUENCE: 2
QFFGHRT                                                                     7

SEQ ID NO: 3            moltype = AA   length = 7
FEATURE                 Location/Qualifiers
source                  1..7
                        mol_type = protein
                        organism = synthetic construct
SEQUENCE: 3
RYSDQYW                                                                     7

SEQ ID NO: 4            moltype = AA   length = 7
FEATURE                 Location/Qualifiers
source                  1..7
                        mol_type = protein
                        organism = synthetic construct
SEQUENCE: 4
QTFSQYT                                                                     7

SEQ ID NO: 5            moltype = AA   length = 7
FEATURE                 Location/Qualifiers
source                  1..7
                        mol_type = protein
                        organism = synthetic construct
SEQUENCE: 5
RTSGHYY                                                                     7

SEQ ID NO: 6            moltype = AA   length = 7
FEATURE                 Location/Qualifiers
source                  1..7
                        mol_type = protein
                        organism = synthetic construct
SEQUENCE: 6
QTFSHYV                                                                     7

SEQ ID NO: 7            moltype = AA   length = 7
FEATURE                 Location/Qualifiers
source                  1..7
                        mol_type = protein
                        organism = synthetic construct
SEQUENCE: 7
RTFGWRR                                                                     7
```

-continued

```
SEQ ID NO: 8           moltype = AA   length = 7
FEATURE                Location/Qualifiers
source                 1..7
                       mol_type = protein
                       organism = synthetic construct
SEQUENCE: 8
SSYSGST                                                                  7

SEQ ID NO: 9           moltype = AA   length = 7
FEATURE                Location/Qualifiers
source                 1..7
                       mol_type = protein
                       organism = synthetic construct
SEQUENCE: 9
GAFGETR                                                                  7

SEQ ID NO: 10          moltype = AA   length = 7
FEATURE                Location/Qualifiers
source                 1..7
                       mol_type = protein
                       organism = synthetic construct
SEQUENCE: 10
RYASSWR                                                                  7

SEQ ID NO: 11          moltype = AA   length = 7
FEATURE                Location/Qualifiers
source                 1..7
                       mol_type = protein
                       organism = synthetic construct
SEQUENCE: 11
RYASDYR                                                                  7

SEQ ID NO: 12          moltype = AA   length = 7
FEATURE                Location/Qualifiers
source                 1..7
                       mol_type = protein
                       organism = synthetic construct
SEQUENCE: 12
RYFSGQR                                                                  7

SEQ ID NO: 13          moltype = AA   length = 7
FEATURE                Location/Qualifiers
source                 1..7
                       mol_type = protein
                       organism = synthetic construct
SEQUENCE: 13
RAFGIYR                                                                  7

SEQ ID NO: 14          moltype = AA   length = 7
FEATURE                Location/Qualifiers
source                 1..7
                       mol_type = protein
                       organism = synthetic construct
SEQUENCE: 14
GTFQEQY                                                                  7

SEQ ID NO: 15          moltype = AA   length = 7
FEATURE                Location/Qualifiers
source                 1..7
                       mol_type = protein
                       organism = synthetic construct
SEQUENCE: 15
TAYGWSR                                                                  7

SEQ ID NO: 16          moltype = AA   length = 7
FEATURE                Location/Qualifiers
source                 1..7
                       mol_type = protein
                       organism = synthetic construct
SEQUENCE: 16
TFDQRSR                                                                  7

SEQ ID NO: 17          moltype = AA   length = 7
FEATURE                Location/Qualifiers
source                 1..7
                       mol_type = protein
                       organism = synthetic construct
SEQUENCE: 17
RFDGELR                                                                  7
```

```
SEQ ID NO: 18              moltype = AA   length = 7
FEATURE                    Location/Qualifiers
source                     1..7
                           mol_type = protein
                           organism = synthetic construct
SEQUENCE: 18
GSFSSTA                                                                   7

SEQ ID NO: 19              moltype = AA   length = 7
FEATURE                    Location/Qualifiers
source                     1..7
                           mol_type = protein
                           organism = synthetic construct
SEQUENCE: 19
HSSGASR                                                                   7

SEQ ID NO: 20              moltype = AA   length = 7
FEATURE                    Location/Qualifiers
source                     1..7
                           mol_type = protein
                           organism = synthetic construct
SEQUENCE: 20
RAFGIYR                                                                   7

SEQ ID NO: 21              moltype = AA   length = 7
FEATURE                    Location/Qualifiers
source                     1..7
                           mol_type = protein
                           organism = synthetic construct
SEQUENCE: 21
STFSGDR                                                                   7

SEQ ID NO: 22              moltype = AA   length = 7
FEATURE                    Location/Qualifiers
source                     1..7
                           mol_type = protein
                           organism = synthetic construct
SEQUENCE: 22
SAFDDVP                                                                   7

SEQ ID NO: 23              moltype = AA   length = 7
FEATURE                    Location/Qualifiers
source                     1..7
                           mol_type = protein
                           organism = synthetic construct
SEQUENCE: 23
STFQGYR                                                                   7

SEQ ID NO: 24              moltype = AA   length = 7
FEATURE                    Location/Qualifiers
source                     1..7
                           mol_type = protein
                           organism = synthetic construct
SEQUENCE: 24
TAFGQYR                                                                   7

SEQ ID NO: 25              moltype = AA   length = 7
FEATURE                    Location/Qualifiers
source                     1..7
                           mol_type = protein
                           organism = synthetic construct
SEQUENCE: 25
GTFGQWR                                                                   7

SEQ ID NO: 26              moltype = AA   length = 8
FEATURE                    Location/Qualifiers
source                     1..8
                           mol_type = protein
                           organism = synthetic construct
SEQUENCE: 26
DWSQDHTL                                                                  8

SEQ ID NO: 27              moltype = AA   length = 8
FEATURE                    Location/Qualifiers
source                     1..8
                           mol_type = protein
                           organism = synthetic construct
SEQUENCE: 27
```

```
SWSGGSKY                                                                        8

SEQ ID NO: 28           moltype = AA  length = 8
FEATURE                 Location/Qualifiers
source                  1..8
                        mol_type = protein
                        organism = synthetic construct SEQUENCE: 28
SASGRRTY                                                                        8

SEQ ID NO: 29           moltype = AA  length = 8
FEATURE                 Location/Qualifiers
source                  1..8
                        mol_type = protein
                        organism = synthetic construct SEQUENCE: 29
RGQAGYTY                                                                        8

SEQ ID NO: 30           moltype = AA  length = 8
FEATURE                 Location/Qualifiers
source                  1..8
                        mol_type = protein
                        organism = synthetic construct SEQUENCE: 30
SASGRPTL                                                                        8

SEQ ID NO: 31           moltype = AA  length = 8
FEATURE                 Location/Qualifiers
source                  1..8
                        mol_type = protein
                        organism = synthetic construct SEQUENCE: 31
GTRSARKR                                                                        8

SEQ ID NO: 32           moltype = AA  length = 8
FEATURE                 Location/Qualifiers
source                  1..8
                        mol_type = protein
                        organism = synthetic construct SEQUENCE: 32
SSSDGFVY                                                                        8

SEQ ID NO: 33           moltype = AA  length = 8
FEATURE                 Location/Qualifiers
source                  1..8
                        mol_type = protein
                        organism = synthetic construct SEQUENCE: 33
GTTDFDQY                                                                        8

SEQ ID NO: 34           moltype = AA  length = 8
FEATURE                 Location/Qualifiers
source                  1..8
                        mol_type = protein
                        organism = synthetic construct SEQUENCE: 34
AADSGTDT                                                                        8

SEQ ID NO: 35           moltype = AA  length = 8
FEATURE                 Location/Qualifiers
source                  1..8
                        mol_type = protein
                        organism = synthetic construct SEQUENCE: 35
QGYQRFRT                                                                        8

SEQ ID NO: 36           moltype = AA  length = 8
FEATURE                 Location/Qualifiers
source                  1..8
                        mol_type = protein
                        organism = synthetic construct SEQUENCE: 36
SWSGGSAR                                                                        8

SEQ ID NO: 37           moltype = AA  length = 8
FEATURE                 Location/Qualifiers
source                  1..8
                        mol_type = protein
                        organism = synthetic construct
```

```
SEQUENCE: 37
AGRDGRDY                                                                      8

SEQ ID NO: 38           moltype = AA  length = 8
FEATURE                 Location/Qualifiers
source                  1..8
                        mol_type = protein
                        organism = synthetic construct
SEQUENCE: 38
GGDAGHTR                                                                      8

SEQ ID NO: 39           moltype = AA  length = 8
FEATURE                 Location/Qualifiers
source                  1..8
                        mol_type = protein
                        organism = synthetic construct
SEQUENCE: 39
SSSDGTYY                                                                      8

SEQ ID NO: 40           moltype = AA  length = 8
FEATURE                 Location/Qualifiers
source                  1..8
                        mol_type = protein
                        organism = synthetic construct
SEQUENCE: 40
RASAGYAQ                                                                      8

SEQ ID NO: 41           moltype = AA  length = 8
FEATURE                 Location/Qualifiers
source                  1..8
                        mol_type = protein
                        organism = synthetic construct
SEQUENCE: 41
SWSDGSRK                                                                      8

SEQ ID NO: 42           moltype = AA  length = 8
FEATURE                 Location/Qualifiers
source                  1..8
                        mol_type = protein
                        organism = synthetic construct
SEQUENCE: 42
TWAGDSAR                                                                      8

SEQ ID NO: 43           moltype = AA  length = 8
FEATURE                 Location/Qualifiers
source                  1..8
                        mol_type = protein
                        organism = synthetic construct
SEQUENCE: 43
SRRGYSTY                                                                      8

SEQ ID NO: 44           moltype = AA  length = 8
FEATURE                 Location/Qualifiers
source                  1..8
                        mol_type = protein
                        organism = synthetic construct
SEQUENCE: 44
SSSDGFVY                                                                      8

SEQ ID NO: 45           moltype = AA  length = 8
FEATURE                 Location/Qualifiers
source                  1..8
                        mol_type = protein
                        organism = synthetic construct
SEQUENCE: 45
GGDAGHTR                                                                      8

SEQ ID NO: 46           moltype = AA  length = 8
FEATURE                 Location/Qualifiers
source                  1..8
                        mol_type = protein
                        organism = synthetic construct
SEQUENCE: 46
TQSQGTTA                                                                      8

SEQ ID NO: 47           moltype = AA  length = 8
FEATURE                 Location/Qualifiers
source                  1..8
                        mol_type = protein
```

```
                            -continued organism = synthetic construct
SEQUENCE: 47
DWQGGWTD                                                                 8

SEQ ID NO: 48           moltype = AA   length = 8
FEATURE                 Location/Qualifiers
source                  1..8
                        mol_type = protein
                        organism = synthetic construct
SEQUENCE: 48
SWRGGSQR                                                                 8

SEQ ID NO: 49           moltype = AA   length = 8
FEATURE                 Location/Qualifiers
source                  1..8
                        mol_type = protein
                        organism = synthetic construct
SEQUENCE: 49
SWSGGSAR                                                                 8

SEQ ID NO: 50           moltype = AA   length = 8
FEATURE                 Location/Qualifiers
source                  1..8
                        mol_type = protein
                        organism = synthetic construct
SEQUENCE: 50
GGDAGHTR                                                                 8

SEQ ID NO: 51           moltype = AA   length = 9
FEATURE                 Location/Qualifiers
source                  1..9
                        mol_type = protein
                        organism = synthetic construct
SEQUENCE: 51
YRDLKQETT                                                                9

SEQ ID NO: 52           moltype = AA   length = 9
FEATURE                 Location/Qualifiers
source                  1..9
                        mol_type = protein
                        organism = synthetic construct
SEQUENCE: 52
VRFNHSRGS                                                                9

SEQ ID NO: 53           moltype = AA   length = 12
FEATURE                 Location/Qualifiers
source                  1..12
                        mol_type = protein
                        organism = synthetic construct
SEQUENCE: 53
SWWRRRHKLD IR                                                           12

SEQ ID NO: 54           moltype = AA   length = 9
FEATURE                 Location/Qualifiers
source                  1..9
                        mol_type = protein
                        organism = synthetic construct
SEQUENCE: 54
FPNHHRRDL                                                                9

SEQ ID NO: 55           moltype = AA   length = 9
FEATURE                 Location/Qualifiers
source                  1..9
                        mol_type = protein
                        organism = synthetic construct
SEQUENCE: 55
HYRYKGPRR                                                                9

SEQ ID NO: 56           moltype = AA   length = 12
FEATURE                 Location/Qualifiers
source                  1..12
                        mol_type = protein
                        organism = synthetic construct
SEQUENCE: 56
LWWGLGDARN KG                                                           12

SEQ ID NO: 57           moltype = AA   length = 9
FEATURE                 Location/Qualifiers
source                  1..9
```

```
                              mol_type = protein
                              organism = synthetic construct
SEQUENCE: 57
DAQLPPEGP                                                                   9

SEQ ID NO: 58                 moltype = AA  length = 15
FEATURE                       Location/Qualifiers
source                        1..15
                              mol_type = protein
                              organism = synthetic construct
SEQUENCE: 58
TFNHSLASKL FNDIK                                                           15

SEQ ID NO: 59                 moltype = AA  length = 9
FEATURE                       Location/Qualifiers
source                        1..9
                              mol_type = protein
                              organism = synthetic construct
SEQUENCE: 59
GIKPDVGRY                                                                   9

SEQ ID NO: 60                 moltype = AA  length = 9
FEATURE                       Location/Qualifiers
source                        1..9
                              mol_type = protein
                              organism = synthetic construct
SEQUENCE: 60
VRTDNGEFA                                                                   9

SEQ ID NO: 61                 moltype = AA  length = 12
FEATURE                       Location/Qualifiers
source                        1..12
                              mol_type = protein
                              organism = synthetic construct
SEQUENCE: 61
SWHVEDLTLS EW                                                              12

SEQ ID NO: 62                 moltype = AA  length = 9
FEATURE                       Location/Qualifiers
source                        1..9
                              mol_type = protein
                              organism = synthetic construct
SEQUENCE: 62
RAYDDAIHQ                                                                   9

SEQ ID NO: 63                 moltype = AA  length = 12
FEATURE                       Location/Qualifiers
source                        1..12
                              mol_type = protein
                              organism = synthetic construct
SEQUENCE: 63
YCDYNGVVPF FK                                                              12

SEQ ID NO: 64                 moltype = AA  length = 12
FEATURE                       Location/Qualifiers
source                        1..12
                              mol_type = protein
                              organism = synthetic construct
SEQUENCE: 64
ITRNYREPTP GR                                                              12

SEQ ID NO: 65                 moltype = AA  length = 9
FEATURE                       Location/Qualifiers
source                        1..9
                              mol_type = protein
                              organism = synthetic construct
SEQUENCE: 65
IGPHYDIRS                                                                   9

SEQ ID NO: 66                 moltype = AA  length = 12
FEATURE                       Location/Qualifiers
source                        1..12
                              mol_type = protein
                              organism = synthetic construct
SEQUENCE: 66
AFFADAYTIP FY                                                              12

SEQ ID NO: 67                 moltype = AA  length = 15
FEATURE                       Location/Qualifiers
```

```
source                         1..15
                               mol_type = protein
                               organism = synthetic construct
SEQUENCE: 67
SADLQNIWPG EHSKW                                                            15

SEQ ID NO: 68                  moltype = AA   length = 15
FEATURE                        Location/Qualifiers
source                         1..15
                               mol_type = protein
                               organism = synthetic construct
SEQUENCE: 68
HGKRSENIHT RAFYG                                                            15

SEQ ID NO: 69                  moltype = AA   length = 15
FEATURE                        Location/Qualifiers
source                         1..15
                               mol_type = protein
                               organism = synthetic construct
SEQUENCE: 69
ARHFNDHYDD YANAW                                                            15

SEQ ID NO: 70                  moltype = AA   length = 12
FEATURE                        Location/Qualifiers
source                         1..12
                               mol_type = protein
                               organism = synthetic construct
SEQUENCE: 70
YWDYNGGVPF FK                                                               12

SEQ ID NO: 71                  moltype = AA   length = 15
FEATURE                        Location/Qualifiers
source                         1..15
                               mol_type = protein
                               organism = synthetic construct
SEQUENCE: 71
GRSIVETDGH SIIRY                                                            15

SEQ ID NO: 72                  moltype = AA   length = 9
FEATURE                        Location/Qualifiers
source                         1..9
                               mol_type = protein
                               organism = synthetic construct
SEQUENCE: 72
RFNPINPHT                                                                   9

SEQ ID NO: 73                  moltype = AA   length = 12
FEATURE                        Location/Qualifiers
source                         1..12
                               mol_type = protein
                               organism = synthetic construct
SEQUENCE: 73
TIIHDQKDTP YY                                                               12

SEQ ID NO: 74                  moltype = AA   length = 12
FEATURE                        Location/Qualifiers
source                         1..12
                               mol_type = protein
                               organism = synthetic construct
SEQUENCE: 74
TWYYLEHLGE YR                                                               12

SEQ ID NO: 75                  moltype = AA   length = 9
FEATURE                        Location/Qualifiers
source                         1..9
                               mol_type = protein
                               organism = synthetic construct
SEQUENCE: 75
RRDLAGAQY                                                                   9

SEQ ID NO: 76                  moltype = AA   length = 119
FEATURE                        Location/Qualifiers
source                         1..119
                               mol_type = protein
                               organism = synthetic construct
SEQUENCE: 76
EVQLQASGGG FVQPGGSLRL SCAASGHYDG ILDMGWFRQA PGKEREFVSA ISDWSQDHTL           60
YADSVKGRFT ISRDNSKNTV YLQMNSLRAE DTATYYCAYR DLKQETTYWG QGTQVTVSS            119
```

```
SEQ ID NO: 77              moltype = AA   length = 119
FEATURE                    Location/Qualifiers
source                     1..119
                           mol_type = protein
                           organism = synthetic construct
SEQUENCE: 77
EVQLQASGGG FVQPGGSLRL SCAASGQFFG HRTMGWFRQA PGKEREFVSA ISSWSGGSKY   60
YADSVKGRFT ISRDNSKNTV YLQMNSLRAE DTATYYCAVR FNHSRGSYWG QGTQVTVSS   119

SEQ ID NO: 78              moltype = AA   length = 122
FEATURE                    Location/Qualifiers
source                     1..122
                           mol_type = protein
                           organism = synthetic construct
SEQUENCE: 78
EVQLQASGGG FVQPGGSLRL SCAASGRYSD QYWMGWFRQA PGKEREFVSA ISSASGRRTY   60
YADSVKGRFT ISRDNSKNTV YLQMNSLRAE DTATYYCASW WRRRHKLDIR YWGQGTQVTV  120
SS                                                                122

SEQ ID NO: 79              moltype = AA   length = 119
FEATURE                    Location/Qualifiers
source                     1..119
                           mol_type = protein
                           organism = synthetic construct
SEQUENCE: 79
EVQLQASGGG FVQPGGSLRL SCAASGQTFS QYTMGWFRQA PGKEREFVSA ISRGQAGYTY   60
YADSVKGRFT ISRDNSKNTV YLQMNSLRAE DTATYYCAFP NHHRRDLYWG QGTQVTVSS   119

SEQ ID NO: 80              moltype = AA   length = 119
FEATURE                    Location/Qualifiers
source                     1..119
                           mol_type = protein
                           organism = synthetic construct
SEQUENCE: 80
EVQLQASGGG FVQPGGSLRL SCAASGRTSG HYYMGWFRQA PGKEREFVSA ISSASGRPTL   60
YADSVKGRFT ISRDNSKNTV YLQMNSLRAE DTATYYCAHY RYKGPRRYWG QGTQVTVSS   119

SEQ ID NO: 81              moltype = AA   length = 122
FEATURE                    Location/Qualifiers
source                     1..122
                           mol_type = protein
                           organism = synthetic construct
SEQUENCE: 81
EVQLQASGGG FVQPGGSLRL SCAASGQTFS HYVMGWFRQA PGKEREFVSA ISGTRSARKR   60
YADSVKGRFT ISRDNSKNTV YLQMNSLRAE DTATYYCALW WGLGDARNKG YWGQGTQVTV  120
SS                                                                122

SEQ ID NO: 82              moltype = AA   length = 119
FEATURE                    Location/Qualifiers
source                     1..119
                           mol_type = protein
                           organism = synthetic construct
SEQUENCE: 82
EVQLQASGGG FVQPGGSLRL SCAASGRTFG WRRMGWFRQA PGKEREFVSA ISSSSDGFVY   60
YADSVKGRFT ISRDNSKNTV YLQMNSLRAE DTATYYCADA QLPPEGPYWG QGTQVTVSS   119

SEQ ID NO: 83              moltype = AA   length = 125
FEATURE                    Location/Qualifiers
source                     1..125
                           mol_type = protein
                           organism = synthetic construct
SEQUENCE: 83
EVQLQASGGG FVQPGGSLRL SCAASGSSYS GSTMGWFRQA PGKEREFVSA ISGTTDFDQY   60
YADSVKGRFT ISRDNSKNTV YLQMNSLRAE DTATYYCATF NHSLASKLFN DIKYWGQGTQ  120
VTVSS                                                             125

SEQ ID NO: 84              moltype = AA   length = 119
FEATURE                    Location/Qualifiers
source                     1..119
                           mol_type = protein
                           organism = synthetic construct
SEQUENCE: 84
EVQLQASGGG FVQPGGSLRL SCAASGGAFG ETRMGWFRQA PGKEREFVSA ISAADSGTDT   60
YADSVKGRFT ISRDNSKNTV YLQMNSLRAE DTATYYCAGI KPDVGRYYWG QGTQVTVSS   119

SEQ ID NO: 85              moltype = AA   length = 119
FEATURE                    Location/Qualifiers
source                     1..119
                           mol_type = protein
```

```
                                    organism   =  synthetic construct
SEQUENCE: 85
EVQLQASGGG FVQPGGSLRL SCAASGRYAS SWRMGWFRQA PGKEREFVSA ISQGYQRFRT      60
YADSVKGRFT ISRDNSKNTV YLQMNSLRAE DTATYYCAVR TDNGEFAYWG QGTQVTVSS      119

SEQ ID NO: 86             moltype = AA   length = 122
FEATURE                   Location/Qualifiers
source                    1..122
                          mol_type = protein
                          organism = synthetic construct
SEQUENCE: 86
EVQLQASGGG FVQPGGSLRL SCAASGRYAS DYRMGWFRQA PGKEREFVSA ISSWSGGSAR      60
YADSVKGRFT ISRDNSKNTV YLQMNSLRAE DTATYYCASW HVEDLTLSEW YWGQGTQVTV     120
SS                                                                   122

SEQ ID NO: 87             moltype = AA   length = 119
FEATURE                   Location/Qualifiers
source                    1..119
                          mol_type = protein
                          organism = synthetic construct
SEQUENCE: 87
EVQLQASGGG FVQPGGSLRL SCAASGRYFS GQRMGWFRQA PGKEREFVSA ISAGRDGRDY      60
YADSVKGRFT ISRDNSKNTV YLQMNSLRAE DTATYYCARA YDDAIHQYWG QGTQVTVSS      119

SEQ ID NO: 88             moltype = AA   length = 122
FEATURE                   Location/Qualifiers
source                    1..122
                          mol_type = protein
                          organism = synthetic construct
SEQUENCE: 88
EVQLQASGGG FVQPGGSLRL SCAASGRAFG IYRMGWFRQA PGKEREFVSA ISGGDAGHTR      60
YADSVKGRFT ISRDNSKNTV YLQMNSLRAE DTATYYCAYC DYNGVVPFFK YWGQGTQVTV     120
SS                                                                   122

SEQ ID NO: 89             moltype = AA   length = 122
FEATURE                   Location/Qualifiers
source                    1..122
                          mol_type = protein
                          organism = synthetic construct
SEQUENCE: 89
EVQLQASGGG FVQPGGSLRL SCAASGGTFQ EQYMGWFRQA PGKEREFVSA ISSSSDGTYY      60
YADSVKGRFT ISRDNSKNTV YLQMNSLRAE DTATYYCAIT RNYREPTPGR YWGQGTQVTV     120
SS                                                                   122

SEQ ID NO: 90             moltype = AA   length = 119
FEATURE                   Location/Qualifiers
source                    1..119
                          mol_type = protein
                          organism = synthetic construct
SEQUENCE: 90
EVQLQASGGG FVQPGGSLRL SCAASGTAYG WSRMGWFRQA PGKEREFVSA ISRASAGYAQ      60
YADSVKGRFT ISRDNSKNTV YLQMNSLRAE DTATYYCAIG PHYDIRSYWG QGTQVTVSS      119

SEQ ID NO: 91             moltype = AA   length = 122
FEATURE                   Location/Qualifiers
source                    1..122
                          mol_type = protein
                          organism = synthetic construct
SEQUENCE: 91
EVQLQASGGG FVQPGGSLRL SCAASGTFDQ RSRMGWFRQA PGKEREFVSA ISSWSDGSRK      60
YADSVKGRFT ISRDNSKNTV YLQMNSLRAE DTATYYCAAF FADAYTIPFY YWGQGTQVTV     120
SS                                                                   122

SEQ ID NO: 92             moltype = AA   length = 125
FEATURE                   Location/Qualifiers
source                    1..125
                          mol_type = protein
                          organism = synthetic construct
SEQUENCE: 92
EVQLQASGGG FVQPGGSLRL SCAASGRFDG ELRMGWFRQA PGKEREFVSA ISTWAGDSAR      60
YADSVKGRFT ISRDNSKNTV YLQMNSLRAE DTATYYCASA DLQNIWPGEH SKWYWGQGTQ    120
VTVSS                                                                125

SEQ ID NO: 93             moltype = AA   length = 125
FEATURE                   Location/Qualifiers
source                    1..125
                          mol_type = protein
                          organism = synthetic construct
SEQUENCE: 93
```

```
EVQLQASGGG FVQPGGSLRL SCAASGGSFS STAMGWFRQA PGKEREFVSA ISSRRGYSTY    60
YADSVKGRFT ISRDNSKNTV YLQMNSLRAE DTATYYCAHG KRSENIHTRA FYGYWGQGTQ   120
VTVSS                                                              125

SEQ ID NO: 94           moltype = AA   length = 125
FEATURE                 Location/Qualifiers
source                  1..125
                        mol_type = protein
                        organism = synthetic construct
SEQUENCE: 94
EVQLQASGGG FVQPGGSLRL SCAASGHSSG ASRMGWFRQA PGKEREFVSA ISSSSDGFVY    60
YADSVKGRFT ISRDNSKNTV YLQMNSLRAE DTATYYCAAR HFNDHYDDYA NAWYWGQGTQ   120
VTVSS                                                              125

SEQ ID NO: 95           moltype = AA   length = 122
FEATURE                 Location/Qualifiers
source                  1..122
                        mol_type = protein
                        organism = synthetic construct
SEQUENCE: 95
EVQLQASGGG FVQPGGSLRL SCAASGRAFG IYRMGWFRQA PGKEREFVSA ISGGDAGHTR    60
YADSVKGRFT ISRDNSKNTV YLQMNSLRAE DTATYYCAYW DYNGGVPFFK YWGQGTQVTV   120
SS                                                                 122

SEQ ID NO: 96           moltype = AA   length = 125
FEATURE                 Location/Qualifiers
source                  1..125
                        mol_type = protein
                        organism = synthetic construct
SEQUENCE: 96
EVQLQASGGG FVQPGGSLRL SCAASGSTFS GDRMGWFRQA PGKEREFVSA ISTQSQGTTA    60
YADSVKGRFT ISRDNSKNTV YLQMNSLRAE DTATYYCAGR SIVETDGHSI IRYYWGQGTQ   120
VTVSS                                                              125

SEQ ID NO: 97           moltype = AA   length = 119
FEATURE                 Location/Qualifiers
source                  1..119
                        mol_type = protein
                        organism = synthetic construct
SEQUENCE: 97
EVQLQASGGG FVQPGGSLRL SCAASGSAFD DVPMGWFRQA PGKEREFVSA ISDWQGGWTD    60
YADSVKGRFT ISRDNSKNTV YLQMNSLRAE DTATYYCARF NPINPHTYWG QGTQVTVSS    119

SEQ ID NO: 98           moltype = AA   length = 122
FEATURE                 Location/Qualifiers
source                  1..122
                        mol_type = protein
                        organism = synthetic construct
SEQUENCE: 98
EVQLQASGGG FVQPGGSLRL SCAASGSTFQ GYRMGWFRQA PGKEREFVSA ISSWRGGSQR    60
YADSVKGRFT ISRDNSKNTV YLQMNSLRAE DTATYYCATI IHDQKDTPYY YWGQGTQVTV   120
SS                                                                 122

SEQ ID NO: 99           moltype = AA   length = 122
FEATURE                 Location/Qualifiers
source                  1..122
                        mol_type = protein
                        organism = synthetic construct
SEQUENCE: 99
EVQLQASGGG FVQPGGSLRL SCAASGTAFG QYRMGWFRQA PGKEREFVSA ISSWSGGSAR    60
YADSVKGRFT ISRDNSKNTV YLQMNSLRAE DTATYYCATW YYLEHLGEYR YWGQGTQVTV   120
SS                                                                 122

SEQ ID NO: 100          moltype = AA   length = 119
FEATURE                 Location/Qualifiers
source                  1..119
                        mol_type = protein
                        organism = synthetic construct
SEQUENCE: 100
EVQLQASGGG FVQPGGSLRL SCAASGGTFG QWRMGWFRQA PGKEREFVSA ISGGDAGHTR    60
YADSVKGRFT ISRDNSKNTV YLQMNSLRAE DTATYYCARR DLAGAQYYWG QGTQVTVSS    119

SEQ ID NO: 101          moltype =      length =
SEQUENCE: 101
000

SEQ ID NO: 102          moltype =      length =
SEQUENCE: 102
000
```

| | | |
|---|---|---|
| SEQ ID NO: 103 SEQUENCE: 103 | moltype = | length = 000 |
| SEQ ID NO: 104 SEQUENCE: 104 | moltype = | length = 000 |
| SEQ ID NO: 105 SEQUENCE: 105 | moltype = | length = 000 |
| SEQ ID NO: 106 SEQUENCE: 106 | moltype = | length = 000 |
| SEQ ID NO: 107 SEQUENCE: 107 | moltype = | length = 000 |
| SEQ ID NO: 108 SEQUENCE: 108 | moltype = | length = 000 |
| SEQ ID NO: 109 SEQUENCE: 109 | moltype = | length = 000 |
| SEQ ID NO: 110 SEQUENCE: 110 | moltype = | length = 000 |
| SEQ ID NO: 111 SEQUENCE: 111 | moltype = | length = 000 |
| SEQ ID NO: 112 SEQUENCE: 112 | moltype = | length = 000 |
| SEQ ID NO: 113 SEQUENCE: 113 | moltype = | length = 000 |
| SEQ ID NO: 114 SEQUENCE: 114 | moltype = | length = 000 |
| SEQ ID NO: 115 SEQUENCE: 115 | moltype = | length = 000 |
| SEQ ID NO: 116 SEQUENCE: 116 | moltype = | length = 000 |
| SEQ ID NO: 117 SEQUENCE: 117 | moltype = | length = 000 |
| SEQ ID NO: 118 SEQUENCE: 118 | moltype = | length = 000 |
| SEQ ID NO: 119 SEQUENCE: 119 | moltype = | length = 000 |
| SEQ ID NO: 120 SEQUENCE: 120 | moltype = | length = 000 |
| SEQ ID NO: 121 SEQUENCE: 121 | moltype = | length = 000 |
| SEQ ID NO: 122 SEQUENCE: 122 | moltype = | length = |

000

SEQ ID NO: 123             moltype =    length =
SEQUENCE: 123
000

SEQ ID NO: 124             moltype =    length =
SEQUENCE: 124
000

SEQ ID NO: 125             moltype =    length =
SEQUENCE: 125
000

SEQ ID NO: 126             moltype =    length =
SEQUENCE: 126
000

SEQ ID NO: 127             moltype =    length =
SEQUENCE: 127
000

SEQ ID NO: 128             moltype =    length =
SEQUENCE: 128
000

SEQ ID NO: 129             moltype =    length =
SEQUENCE: 129
000

SEQ ID NO: 130             moltype =    length =
SEQUENCE: 130
000

SEQ ID NO: 131             moltype =    length =
SEQUENCE: 131
000

SEQ ID NO: 132             moltype =    length =
SEQUENCE: 132
000

SEQ ID NO: 133             moltype =    length =
SEQUENCE: 133
000

SEQ ID NO: 134             moltype =    length =
SEQUENCE: 134
000

SEQ ID NO: 135             moltype =    length =
SEQUENCE: 135
000

SEQ ID NO: 136             moltype =    length =
SEQUENCE: 136
000

SEQ ID NO: 137             moltype =    length =
SEQUENCE: 137
000

SEQ ID NO: 138             moltype =    length =
SEQUENCE: 138
000

SEQ ID NO: 139             moltype =    length =
SEQUENCE: 139
000

SEQ ID NO: 140             moltype =    length =
SEQUENCE: 140
000

SEQ ID NO: 141             moltype =    length =
SEQUENCE: 141
000

SEQ ID NO: 142             moltype =    length =

-continued

```
SEQUENCE: 142
000

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype =    length =
SEQUENCE: 147
000

SEQ ID NO: 148          moltype =    length =
SEQUENCE: 148
000

SEQ ID NO: 149          moltype =    length =
SEQUENCE: 149
000

SEQ ID NO: 150          moltype =    length =
SEQUENCE: 150
000

SEQ ID NO: 151          moltype =    length =
SEQUENCE: 151
000

SEQ ID NO: 152          moltype =    length =
SEQUENCE: 152
000

SEQ ID NO: 153          moltype =    length =
SEQUENCE: 153
000

SEQ ID NO: 154          moltype =    length =
SEQUENCE: 154
000

SEQ ID NO: 155          moltype =    length =
SEQUENCE: 155
000

SEQ ID NO: 156          moltype =    length =
SEQUENCE: 156
000

SEQ ID NO: 157          moltype =    length =
SEQUENCE: 157
000

SEQ ID NO: 158          moltype =    length =
SEQUENCE: 158
000

SEQ ID NO: 159          moltype =    length =
SEQUENCE: 159
000

SEQ ID NO: 160          moltype =    length =
SEQUENCE: 160
000

SEQ ID NO: 161          moltype =    length =
SEQUENCE: 161
000
```

| | | |
|---|---|---|
| SEQ ID NO: 162<br>SEQUENCE: 162<br>000 | moltype = | length = |
| SEQ ID NO: 163<br>SEQUENCE: 163<br>000 | moltype = | length = |
| SEQ ID NO: 164<br>SEQUENCE: 164<br>000 | moltype = | length = |
| SEQ ID NO: 165<br>SEQUENCE: 165<br>000 | moltype = | length = |
| SEQ ID NO: 166<br>SEQUENCE: 166<br>000 | moltype = | length = |
| SEQ ID NO: 167<br>SEQUENCE: 167<br>000 | moltype = | length = |
| SEQ ID NO: 168<br>SEQUENCE: 168<br>000 | moltype = | length = |
| SEQ ID NO: 169<br>SEQUENCE: 169<br>000 | moltype = | length = |
| SEQ ID NO: 170<br>SEQUENCE: 170<br>000 | moltype = | length = |
| SEQ ID NO: 171<br>SEQUENCE: 171<br>000 | moltype = | length = |
| SEQ ID NO: 172<br>SEQUENCE: 172<br>000 | moltype = | length = |
| SEQ ID NO: 173<br>SEQUENCE: 173<br>000 | moltype = | length = |
| SEQ ID NO: 174<br>SEQUENCE: 174<br>000 | moltype = | length = |
| SEQ ID NO: 175<br>SEQUENCE: 175<br>000 | moltype = | length = |
| SEQ ID NO: 176<br>SEQUENCE: 176<br>000 | moltype = | length = |
| SEQ ID NO: 177<br>SEQUENCE: 177<br>000 | moltype = | length = |
| SEQ ID NO: 178<br>SEQUENCE: 178<br>000 | moltype = | length = |
| SEQ ID NO: 179<br>SEQUENCE: 179<br>000 | moltype = | length = |
| SEQ ID NO: 180<br>SEQUENCE: 180<br>000 | moltype = | length = |
| SEQ ID NO: 181<br>SEQUENCE: 181<br>000 | moltype = | length = |

```
SEQ ID NO: 182          moltype =    length =
SEQUENCE: 182
000

SEQ ID NO: 183          moltype = AA   length = 98
FEATURE                 Location/Qualifiers
REGION                  1..98
                        note = Synthetic construct
SITE                    27
                        note = MISC_FEATURE - Can be any amino acid or amino acids
                          (e.g., any CDR1 describedherein)
SITE                    47
                        note = MISC_FEATURE - Can be any amino acid or amino acids
                          (e.g., any CDR2 describedherein)
SITE                    86
                        note = MISC_FEATURE - Can be any amino acid or amino acids
                          (e.g., any CDR3 describedherein)
source                  1..98
                        mol_type = protein
                        organism = synthetic construct
SEQUENCE: 183
EVQLQASGGG FVQPGGSLRL SCAASGXMGW FRQAPGKERE FVSAISXYAD SVKGRFTISR   60
DNSKNTVYLQ MNSLRAEDTA TYYCAXYWGQ GTQVTVSS                          98

SEQ ID NO: 184          moltype = AA   length = 98
FEATURE                 Location/Qualifiers
REGION                  1..98
                        note = Synthetic construct
SITE                    27
                        note = MISC_FEATURE - Can be any amino acid or amino acids
                          (e.g., any CDR1 describedherein)
SITE                    47
                        note = MISC_FEATURE - Can be any amino acid or amino acids
                          (e.g., any CDR2 describedherein)
SITE                    86
                        note = MISC_FEATURE - Can be any amino acid or amino acids
                          (e.g., any CDR3 describedherein)
source                  1..98
                        mol_type = protein
                        organism = synthetic construct
SEQUENCE: 184
EVQLQASGGG FVQPGGSLRL SCAASGXMGW FRQAPGKERE FVSAISXYAD SVKGRFTISR   60
DNSKNTVYLQ MNSLRAEDTA TYYCAXYWGQ GTQVTVSS                          98

SEQ ID NO: 185          moltype = AA   length = 99
FEATURE                 Location/Qualifiers
REGION                  1..99
                        note = Synthetic construct
SITE                    27
                        note = MISC_FEATURE - Can be any amino acid or amino acids
                          (e.g., any CDR1 describedherein)
SITE                    47
                        note = MISC_FEATURE - Can be any amino acid or amino acids
                          (e.g., any CDR2 describedherein)
SITE                    87
                        note = MISC_FEATURE - Can be any amino acid or amino acids
                          (e.g., any CDR3 describedherein)
source                  1..99
                        mol_type = protein
                        organism = synthetic construct
SEQUENCE: 185
EVQLQASGGG FVQAGGSLRL SCAASGXMGW FRQAPGKERE FVAAISXYYA DSVKGRFTIS   60
RDNAKNTVYL QMNSLKPEDT ATYYCAXYWG QGTQVTVSS                         99

SEQ ID NO: 186          moltype = AA   length = 99
FEATURE                 Location/Qualifiers
REGION                  1..99
                        note = Synthetic construct
SITE                    27
                        note = MISC_FEATURE - Can be any amino acid or amino acids
                          (e.g., any CDR1 describedherein)
SITE                    47
                        note = MISC_FEATURE - Can be any amino acid or amino acids
                          (e.g., any CDR2 describedherein)
SITE                    87
                        note = MISC_FEATURE - Can be any amino acid or amino acids
                          (e.g., any CDR3 describedherein)
source                  1..99
```

```
                            mol_type = protein
                            organism = synthetic construct
SEQUENCE: 186
EVQLQASGGG FVQAGGSLRL SCAASGXMGW FRQAPGKERE FVAAISXYYA DSVKGRFTIS    60
RDNAKNTVYL QMNSLKPEDT ATYYCAXYWG QGTQVTVSS                           99

SEQ ID NO: 187          moltype =    length =
SEQUENCE: 187
000

SEQ ID NO: 188          moltype =    length =
SEQUENCE: 188
000

SEQ ID NO: 189          moltype =    length =
SEQUENCE: 189
000

SEQ ID NO: 190          moltype = AA   length = 26
FEATURE                 Location/Qualifiers
REGION                  1..26
                        note = Synthetic construct
source                  1..26
                        mol_type = protein
                        organism = synthetic construct
SEQUENCE: 190
EVQLQASGGG FVQAGGSLRL SCAASG                                          26

SEQ ID NO: 191          moltype = AA   length = 26
FEATURE                 Location/Qualifiers
REGION                  1..26
                        note = Synthetic construct
source                  1..26
                        mol_type = protein
                        organism = synthetic construct
SEQUENCE: 191
EVQLQASGGG FVQPGGSLRL SCAASG                                          26

SEQ ID NO: 192          moltype = AA   length = 30
FEATURE                 Location/Qualifiers
REGION                  1..30
                        note = Synthetic construct
source                  1..30
                        mol_type = protein
                        organism = synthetic construct
SEQUENCE: 192
QVQLVESGGG SVQAGGSLRL SCTASGGSEY                                      30

SEQ ID NO: 193          moltype = AA   length = 26
FEATURE                 Location/Qualifiers
REGION                  1..26
                        note = Synthetic construct
source                  1..26
                        mol_type = protein
                        organism = synthetic construct
SEQUENCE: 193
QVQLVESGGG SVQAGGSLRL SCTASG                                          26

SEQ ID NO: 194          moltype = AA   length = 30
FEATURE                 Location/Qualifiers
REGION                  1..30
                        note = Synthetic construct
source                  1..30
                        mol_type = protein
                        organism = synthetic construct
SEQUENCE: 194
QVQLVESGGG SVQAGGSLRL SCTASGFSRE                                      30

SEQ ID NO: 195          moltype = AA   length = 30
FEATURE                 Location/Qualifiers
REGION                  1..30
                        note = Synthetic construct
source                  1..30
                        mol_type = protein
                        organism = synthetic construct
SEQUENCE: 195
QVQLQESGPS LVRPSQTLSL TCTISGFSRE                                      30

SEQ ID NO: 196          moltype = AA   length = 26
```

```
FEATURE                 Location/Qualifiers
REGION                  1..26
                        note = Synthetic construct
source                  1..26
                        mol_type = protein
                        organism = synthetic construct
SEQUENCE: 196
QVQLQESGPS LVRPSQTLSL TCTISG                                        26

SEQ ID NO: 197          moltype = AA   length = 30
FEATURE                 Location/Qualifiers
REGION                  1..30
                        note = Synthetic construct
source                  1..30
                        mol_type = protein
                        organism = synthetic construct
SEQUENCE: 197
QVQLVESGGN LVQPGGSLRL SCAASGFTFG                                    30

SEQ ID NO: 198          moltype = AA   length = 26
FEATURE                 Location/Qualifiers
REGION                  1..26
                        note = Synthetic construct
source                  1..26
                        mol_type = protein
                        organism = synthetic construct
SEQUENCE: 198
QVQLVESGGN LVQPGGSLRL SCAASG                                        26

SEQ ID NO: 199          moltype = AA   length = 30
FEATURE                 Location/Qualifiers
REGION                  1..30
                        note = Synthetic construct
source                  1..30
                        mol_type = protein
                        organism = synthetic construct
SEQUENCE: 199
QVQLVESGGA LVQPGGSLRL SCAASGFPVN                                    30

SEQ ID NO: 200          moltype = AA   length = 30
FEATURE                 Location/Qualifiers
REGION                  1..30
                        note = Synthetic construct
source                  1..30
                        mol_type = protein
                        organism = synthetic construct
SEQUENCE: 200
QVQLVESGGA LVQPGGSLRL SCAASGFTFG                                    30

SEQ ID NO: 201          moltype = AA   length = 30
FEATURE                 Location/Qualifiers
REGION                  1..30
                        note = Synthetic construct
source                  1..30
                        mol_type = protein
                        organism = synthetic construct
SEQUENCE: 201
QVQLVESGGG LVQPGGSLRL SCAASGFTFG                                    30

SEQ ID NO: 202          moltype = AA   length = 26
FEATURE                 Location/Qualifiers
REGION                  1..26
                        note = Synthetic construct
source                  1..26
                        mol_type = protein
                        organism = synthetic construct
SEQUENCE: 202
QVQLVESGGA LVQPGGSLRL SCAASG                                        26

SEQ ID NO: 203          moltype = AA   length = 26
FEATURE                 Location/Qualifiers
REGION                  1..26
                        note = Synthetic construct
source                  1..26
                        mol_type = protein
                        organism = synthetic construct
SEQUENCE: 203
QVQLVESGGG LVQAGGSLRL SCAASG                                        26
```

```
SEQ ID NO: 204              moltype = AA   length = 26
FEATURE                     Location/Qualifiers
REGION                      1..26
                            note = Synthetic construct
source                      1..26
                            mol_type = protein
                            organism = synthetic construct
SEQUENCE: 204
QVQLVESGGG LMQAGGSLRL SCAVSG                                              26

SEQ ID NO: 205              moltype = AA   length = 26
FEATURE                     Location/Qualifiers
REGION                      1..26
                            note = Synthetic construct
source                      1..26
                            mol_type = protein
                            organism = synthetic construct
SEQUENCE: 205
QVQLQESGGG LVQAGGSLRL SCAASG                                              26

SEQ ID NO: 206              moltype = AA   length = 26
FEATURE                     Location/Qualifiers
REGION                      1..26
                            note = Synthetic construct
source                      1..26
                            mol_type = protein
                            organism = synthetic construct
SEQUENCE: 206
HVQLVESGGG LVQAGGSLRL SCAASG                                              26

SEQ ID NO: 207              moltype = AA   length = 26
FEATURE                     Location/Qualifiers
REGION                      1..26
                            note = Synthetic construct
source                      1..26
                            mol_type = protein
                            organism = synthetic construct
SEQUENCE: 207
DVQLVESGGG LVQAGGSLRL SCAASG                                              26

SEQ ID NO: 208              moltype = AA   length = 26
FEATURE                     Location/Qualifiers
REGION                      1..26
                            note = Synthetic construct
source                      1..26
                            mol_type = protein
                            organism = synthetic construct
SEQUENCE: 208
EVQLVESGGG LVQAGGSLRL SCAASG                                              26

SEQ ID NO: 209              moltype = AA   length = 30
FEATURE                     Location/Qualifiers
REGION                      1..30
                            note = Synthetic construct
source                      1..30
                            mol_type = protein
                            organism = synthetic construct
SEQUENCE: 209
EVQLVESGGG VVQPGRSLRL SCAASGFTFD                                          30

SEQ ID NO: 210              moltype = AA   length = 26
FEATURE                     Location/Qualifiers
REGION                      1..26
                            note = Synthetic construct
source                      1..26
                            mol_type = protein
                            organism = synthetic construct
SEQUENCE: 210
EVQLVESGGG VVQPGRSLRL SCAASG                                              26

SEQ ID NO: 211              moltype = AA   length = 30
FEATURE                     Location/Qualifiers
REGION                      1..30
                            note = Synthetic construct
source                      1..30
                            mol_type = protein
                            organism = synthetic construct
SEQUENCE: 211
DVQLQASGGG LVQAGGSLRL SCAASGFKIT                                          30
```

```
SEQ ID NO: 212          moltype = AA  length = 26
FEATURE                 Location/Qualifiers
REGION                  1..26
                        note = Synthetic construct
source                  1..26
                        mol_type = protein
                        organism = synthetic construct
SEQUENCE: 212
DVQLQASGGG LVQAGGSLRL SCAASG                                          26

SEQ ID NO: 213          moltype =    length =
SEQUENCE: 213
000

SEQ ID NO: 214          moltype =    length =
SEQUENCE: 214
000

SEQ ID NO: 215          moltype =    length =
SEQUENCE: 215
000

SEQ ID NO: 216          moltype =    length =
SEQUENCE: 216
000

SEQ ID NO: 217          moltype =    length =
SEQUENCE: 217
000

SEQ ID NO: 218          moltype =    length =
SEQUENCE: 218
000

SEQ ID NO: 219          moltype =    length =
SEQUENCE: 219
000

SEQ ID NO: 220          moltype = AA  length = 19
FEATURE                 Location/Qualifiers
REGION                  1..19
                        note = Synthetic construct
source                  1..19
                        mol_type = protein
                        organism = synthetic construct
SEQUENCE: 220
MGWFRQAPGK EREFVAAIS                                                  19

SEQ ID NO: 221          moltype = AA  length = 19
FEATURE                 Location/Qualifiers
REGION                  1..19
                        note = Synthetic construct
source                  1..19
                        mol_type = protein
                        organism = synthetic construct
SEQUENCE: 221
MGWFRQAPGK EREFVSAIS                                                  19

SEQ ID NO: 222          moltype = AA  length = 14
FEATURE                 Location/Qualifiers
REGION                  1..14
                        note = Synthetic construct
source                  1..14
                        mol_type = protein
                        organism = synthetic construct
SEQUENCE: 222
WFRQAPGQER EAVA                                                       14

SEQ ID NO: 223          moltype = AA  length = 17
FEATURE                 Location/Qualifiers
REGION                  1..17
                        note = Synthetic construct
source                  1..17
                        mol_type = protein
                        organism = synthetic construct
SEQUENCE: 223
WFRQAPGQER EAVAAIA                                                    17
```

```
SEQ ID NO: 224          moltype = AA  length = 14
FEATURE                 Location/Qualifiers
REGION                  1..14
                        note = Synthetic construct
source                  1..14
                        mol_type = protein
                        organism = synthetic construct
SEQUENCE: 224
WVRQAPGKAL EWLG                                                           14

SEQ ID NO: 225          moltype = AA  length = 16
FEATURE                 Location/Qualifiers
REGION                  1..16
                        note = Synthetic construct
source                  1..16
                        mol_type = protein
                        organism = synthetic construct
SEQUENCE: 225
WVRQAPGKAL EWLGRI                                                         16

SEQ ID NO: 226          moltype = AA  length = 14
FEATURE                 Location/Qualifiers
REGION                  1..14
                        note = Synthetic construct
source                  1..14
                        mol_type = protein
                        organism = synthetic construct
SEQUENCE: 226
WFRQAPGQER EWLG                                                           14

SEQ ID NO: 227          moltype = AA  length = 16
FEATURE                 Location/Qualifiers
REGION                  1..16
                        note = Synthetic construct
source                  1..16
                        mol_type = protein
                        organism = synthetic construct
SEQUENCE: 227
WFRQAPGQER EWLGRI                                                         16

SEQ ID NO: 228          moltype = AA  length = 14
FEATURE                 Location/Qualifiers
REGION                  1..14
                        note = Synthetic construct
source                  1..14
                        mol_type = protein
                        organism = synthetic construct
SEQUENCE: 228
WVRQAPGGGL EWVA                                                           14

SEQ ID NO: 229          moltype = AA  length = 14
FEATURE                 Location/Qualifiers
REGION                  1..14
                        note = Synthetic construct
source                  1..14
                        mol_type = protein
                        organism = synthetic construct
SEQUENCE: 229
WYRQATGKER EWVA                                                           14

SEQ ID NO: 230          moltype = AA  length = 16
FEATURE                 Location/Qualifiers
REGION                  1..16
                        note = Synthetic construct
source                  1..16
                        mol_type = protein
                        organism = synthetic construct
SEQUENCE: 230
MSWYRQATGK EREWVA                                                         16

SEQ ID NO: 231          moltype = AA  length = 19
FEATURE                 Location/Qualifiers
REGION                  1..19
                        note = Synthetic construct
source                  1..19
                        mol_type = protein
                        organism = synthetic construct
SEQUENCE: 231
MGWFRQAPGK EREFVAAIR                                                      19
```

| | | |
|---|---|---|
| SEQ ID NO: 232<br>FEATURE<br>REGION<br><br>source | moltype = AA length = 18<br>Location/Qualifiers<br>1..18<br>note = Synthetic construct<br>1..18<br>mol_type = protein<br>organism = synthetic construct | |
| SEQUENCE: 232<br>MGWFRQAPGK EREFVAAI | | 18 |
| SEQ ID NO: 233<br>FEATURE<br>REGION<br><br>source | moltype = AA length = 16<br>Location/Qualifiers<br>1..16<br>note = Synthetic construct<br>1..16<br>mol_type = protein<br>organism = synthetic construct | |
| SEQUENCE: 233<br>MGWFRQAPGK EREFVA | | 16 |
| SEQ ID NO: 234<br>FEATURE<br>REGION<br><br>source | moltype = AA length = 16<br>Location/Qualifiers<br>1..16<br>note = Synthetic construct<br>1..16<br>mol_type = protein<br>organism = synthetic construct | |
| SEQUENCE: 234<br>MGWYRQAPGK ERELVA | | 16 |
| SEQ ID NO: 235<br>FEATURE<br>REGION<br><br>source | moltype = AA length = 17<br>Location/Qualifiers<br>1..17<br>note = Synthetic construct<br>1..17<br>mol_type = protein<br>organism = synthetic construct | |
| SEQUENCE: 235<br>MGWYRQAPGK ERELVAA | | 17 |
| SEQ ID NO: 236<br>FEATURE<br>REGION<br><br>source | moltype = AA length = 19<br>Location/Qualifiers<br>1..19<br>note = Synthetic construct<br>1..19<br>mol_type = protein<br>organism = synthetic construct | |
| SEQUENCE: 236<br>MGWYRQAPGK ERELVAAID | | 19 |
| SEQ ID NO: 237<br>FEATURE<br>REGION<br><br>source | moltype = AA length = 19<br>Location/Qualifiers<br>1..19<br>note = Synthetic construct<br>1..19<br>mol_type = protein<br>organism = synthetic construct | |
| SEQUENCE: 237<br>MGWYRQAPGK ERELVAVIS | | 19 |
| SEQ ID NO: 238<br>FEATURE<br>REGION<br><br>source | moltype = AA length = 16<br>Location/Qualifiers<br>1..16<br>note = Synthetic construct<br>1..16<br>mol_type = protein<br>organism = synthetic construct | |
| SEQUENCE: 238<br>MGWFRQAPGK EREGVA | | 16 |
| SEQ ID NO: 239<br>FEATURE<br>REGION<br><br>source<br><br>SEQUENCE: 239 | moltype = AA length = 14<br>Location/Qualifiers<br>1..14<br>note = Synthetic construct<br>1..14<br>mol_type = protein<br>organism = synthetic construct | |

```
WFRQAPGKER EGVA                                                              14

SEQ ID NO: 240         moltype = AA   length = 16
FEATURE                Location/Qualifiers
REGION                 1..16
                       note = Synthetic construct
source                 1..16
                       mol_type = protein
                       organism = synthetic construct
SEQUENCE: 240
MGWFRQAPGK EREFVA                                                            16

SEQ ID NO: 241         moltype = AA   length = 14
FEATURE                Location/Qualifiers
REGION                 1..14
                       note = Synthetic construct
source                 1..14
                       mol_type = protein
                       organism = synthetic construct
SEQUENCE: 241
WFRQAPGKER EFVA                                                              14

SEQ ID NO: 242         moltype = AA   length = 14
FEATURE                Location/Qualifiers
REGION                 1..14
                       note = Synthetic construct
source                 1..14
                       mol_type = protein
                       organism = synthetic construct
SEQUENCE: 242
WVRQAPGKGP EWVA                                                              14

SEQ ID NO: 243         moltype = AA   length = 14
FEATURE                Location/Qualifiers
REGION                 1..14
                       note = Synthetic construct
source                 1..14
                       mol_type = protein
                       organism = synthetic construct
SEQUENCE: 243
WFRQAPGKER EFVS                                                              14

SEQ ID NO: 244         moltype =      length =
SEQUENCE: 244
000

SEQ ID NO: 245         moltype =      length =
SEQUENCE: 245
000

SEQ ID NO: 246         moltype =      length =
SEQUENCE: 246
000

SEQ ID NO: 247         moltype =      length =
SEQUENCE: 247
000

SEQ ID NO: 248         moltype =      length =
SEQUENCE: 248
000

SEQ ID NO: 249         moltype =      length =
SEQUENCE: 249
000

SEQ ID NO: 250         moltype = AA   length = 38
FEATURE                Location/Qualifiers
REGION                 1..38
                       note = Synthetic construct
source                 1..38
                       mol_type = protein
                       organism = synthetic construct
SEQUENCE: 250
YADSVKGRFT ISRDNAKNTV YLQMNSLKPE DTATYYCA                                    38

SEQ ID NO: 251         moltype = AA   length = 39
FEATURE                Location/Qualifiers
REGION                 1..39
```

```
                        -continued note = Synthetic construct
source                  1..39
                        mol_type = protein
                        organism = synthetic construct
SEQUENCE: 251
YYADSVKGRF TISRDNAKNT VYLQMNSLKP EDTATYYCA                    39

SEQ ID NO: 252          moltype = AA  length = 38
FEATURE                 Location/Qualifiers
REGION                  1..38
                        note = Synthetic construct
source                  1..38
                        mol_type = protein
                        organism = synthetic construct
SEQUENCE: 252
YADSVKGRFT ISRDNSKNTV YLQMNSLRAE DTATYYCA                     38

SEQ ID NO: 253          moltype = AA  length = 39
FEATURE                 Location/Qualifiers
REGION                  1..39
                        note = Synthetic construct
source                  1..39
                        mol_type = protein
                        organism = synthetic construct
SEQUENCE: 253
YYADSVKGRF TISRDNSKNT VYLQMNSLRA EDTATYYCA                    39

SEQ ID NO: 254          moltype = AA  length = 31
FEATURE                 Location/Qualifiers
REGION                  1..31
                        note = Synthetic construct
source                  1..31
                        mol_type = protein
                        organism = synthetic construct
SEQUENCE: 254
RFTISRDNAK NTVTLQMNNL KPEDTAIYYC A                            31

SEQ ID NO: 255          moltype = AA  length = 32
FEATURE                 Location/Qualifiers
REGION                  1..32
                        note = Synthetic construct
source                  1..32
                        mol_type = protein
                        organism = synthetic construct
SEQUENCE: 255
RFTISRDNAK NTVTLQMNNL KPEDTAIYYC AA                           32

SEQ ID NO: 256          moltype = AA  length = 31
FEATURE                 Location/Qualifiers
REGION                  1..31
                        note = Synthetic construct
source                  1..31
                        mol_type = protein
                        organism = synthetic construct
SEQUENCE: 256
RLTITRDISK SQVSLSLSSV TLEDTAEYYC V                            31

SEQ ID NO: 257          moltype = AA  length = 32
FEATURE                 Location/Qualifiers
REGION                  1..32
                        note = Synthetic construct
source                  1..32
                        mol_type = protein
                        organism = synthetic construct
SEQUENCE: 257
RLTITRDISK SQVSLSLSSV TLEDTAEYYC VY                           32

SEQ ID NO: 258          moltype = AA  length = 31
FEATURE                 Location/Qualifiers
REGION                  1..31
                        note = Synthetic construct
source                  1..31
                        mol_type = protein
                        organism = synthetic construct
SEQUENCE: 258
RFTISRDIAK NTVTLQMNNL KPEDTAIYYV Y                            31

SEQ ID NO: 259          moltype = AA  length = 32
FEATURE                 Location/Qualifiers
```

```
REGION                    1..32
                          note = Synthetic construct
source                    1..32
                          mol_type = protein
                          organism = synthetic construct
SEQUENCE: 259
RFTISRDIAK NTVTLQMNNL KPEDTAIYYV YA                                     32

SEQ ID NO: 260            moltype = AA  length = 39
FEATURE                   Location/Qualifiers
REGION                    1..39
                          note = Synthetic construct
source                    1..39
                          mol_type = protein
                          organism = synthetic construct
SEQUENCE: 260
YYADSVKGRF TISRDNAKNT VTLQMNNLKP EDTAIYYCA                              39

SEQ ID NO: 261            moltype = AA  length = 40
FEATURE                   Location/Qualifiers
REGION                    1..40
                          note = Synthetic construct
source                    1..40
                          mol_type = protein
                          organism = synthetic construct
SEQUENCE: 261
YYADSVKGRF TISRDNAKNT VTLQMNNLKP EDTAIYYCAA                             40

SEQ ID NO: 262            moltype = AA  length = 39
FEATURE                   Location/Qualifiers
REGION                    1..39
                          note = Synthetic construct
source                    1..39
                          mol_type = protein
                          organism = synthetic construct
SEQUENCE: 262
YEDSVKGRFC ISRDDARNTV YLQMNSLKPE DTAVYYCNV                              39

SEQ ID NO: 263            moltype = AA  length = 38
FEATURE                   Location/Qualifiers
REGION                    1..38
                          note = Synthetic construct
source                    1..38
                          mol_type = protein
                          organism = synthetic construct
SEQUENCE: 263
YEDSVKGRFC ISRDDARNTV YLQMNSLKPE DTAVYYCN                               38

SEQ ID NO: 264            moltype = AA  length = 39
FEATURE                   Location/Qualifiers
REGION                    1..39
                          note = Synthetic construct
source                    1..39
                          mol_type = protein
                          organism = synthetic construct
SEQUENCE: 264
YADSVKGRFT ISRDNAKNSV YLQMNSLRVE DTAVYYCAR                              39

SEQ ID NO: 265            moltype = AA  length = 38
FEATURE                   Location/Qualifiers
REGION                    1..38
                          note = Synthetic construct
source                    1..38
                          mol_type = protein
                          organism = synthetic construct
SEQUENCE: 265
YADSVKGRFT ISRDNAKNSV YLQMNSLRVE DTAVYYCA                               38

SEQ ID NO: 266            moltype = AA  length = 39
FEATURE                   Location/Qualifiers
REGION                    1..39
                          note = Synthetic construct
source                    1..39
                          mol_type = protein
                          organism = synthetic construct
SEQUENCE: 266
YADSVKGRFT ISRDNARNTV YLQMNSLKPE DTAVYYCAR                              39

SEQ ID NO: 267            moltype = AA  length = 38
```

```
FEATURE              Location/Qualifiers
REGION               1..38
                     note = Synthetic construct
source               1..38
                     mol_type = protein
                     organism = synthetic construct
SEQUENCE: 267
YADSVKGRFT ISRDNARNTV YLQMNSLKPE DTAVYYCA                              38

SEQ ID NO: 268       moltype = AA  length = 39
FEATURE              Location/Qualifiers
REGION               1..39
                     note = Synthetic construct
source               1..39
                     mol_type = protein
                     organism = synthetic construct
SEQUENCE: 268
YADSVKGRFT ISRDNARNTV YLQMNSLKPE DTAVYYCAR                             39

SEQ ID NO: 269       moltype = AA  length = 32
FEATURE              Location/Qualifiers
REGION               1..32
                     note = Synthetic construct
source               1..32
                     mol_type = protein
                     organism = synthetic construct
SEQUENCE: 269
RFTISRDNAR NTVYLQMNSL KPEDTAVYYC AR                                    32

SEQ ID NO: 270       moltype = AA  length = 39
FEATURE              Location/Qualifiers
REGION               1..39
                     note = Synthetic construct
source               1..39
                     mol_type = protein
                     organism = synthetic construct
SEQUENCE: 270
YADSVKGRFT ISRDKGKNTV YLQMDSLKPE DTATYYCAA                             39

SEQ ID NO: 271       moltype = AA  length = 32
FEATURE              Location/Qualifiers
REGION               1..32
                     note = Synthetic construct
source               1..32
                     mol_type = protein
                     organism = synthetic construct
SEQUENCE: 271
RFTISRDKGK NTVYLQMDSL KPEDTATYYC AA                                    32

SEQ ID NO: 272       moltype = AA  length = 38
FEATURE              Location/Qualifiers
REGION               1..38
                     note = Synthetic construct
source               1..38
                     mol_type = protein
                     organism = synthetic construct
SEQUENCE: 272
YADSVKGRFT ISRDKGKNTV YLQMDSLKPE DTATYYCA                              38

SEQ ID NO: 273       moltype = AA  length = 31
FEATURE              Location/Qualifiers
REGION               1..31
                     note = Synthetic construct
source               1..31
                     mol_type = protein
                     organism = synthetic construct
SEQUENCE: 273
RFTISRDKGK NTVYLQMDSL KPEDTATYYC A                                     31

SEQ ID NO: 274       moltype = AA  length = 39
FEATURE              Location/Qualifiers
REGION               1..39
                     note = Synthetic construct
source               1..39
                     mol_type = protein
                     organism = synthetic construct
SEQUENCE: 274
YYADSVKGRF TISRDKAKNT VYLQMNSLKY EDTAVYYCA                             39
```

```
SEQ ID NO: 275          moltype = AA  length = 38
FEATURE                 Location/Qualifiers
REGION                  1..38
                        note = Synthetic construct
source                  1..38
                        mol_type = protein
                        organism = synthetic construct
SEQUENCE: 275
YADSVKGRFT ISRDKAKNTV YLQMNSLKYE DTAVYYCA                              38

SEQ ID NO: 276          moltype = AA  length = 39
FEATURE                 Location/Qualifiers
REGION                  1..39
                        note = Synthetic construct
source                  1..39
                        mol_type = protein
                        organism = synthetic construct
SEQUENCE: 276
YYADSVKGRF TISRDNAKNT VYLQMNSLKP EDTAVYYCA                             39

SEQ ID NO: 277          moltype = AA  length = 39
FEATURE                 Location/Qualifiers
REGION                  1..39
                        note = Synthetic construct
source                  1..39
                        mol_type = protein
                        organism = synthetic construct
SEQUENCE: 277
LHNPALKSRL TITRDISKSQ VSLSLSSVTL EDTAEYYCV                             39

SEQ ID NO: 278          moltype = AA  length = 40
FEATURE                 Location/Qualifiers
REGION                  1..40
                        note = Synthetic construct
source                  1..40
                        mol_type = protein
                        organism = synthetic construct
SEQUENCE: 278
LHNPALKSRL TITRDISKSQ VSLSLSSVTL EDTAEYYCVY                            40

SEQ ID NO: 279          moltype = AA  length = 40
FEATURE                 Location/Qualifiers
REGION                  1..40
                        note = Synthetic construct
source                  1..40
                        mol_type = protein
                        organism = synthetic construct
SEQUENCE: 279
LHNPALKSRF TISRDIAKNT VTLQMNNLKP EDTAIYYVYA                            40

SEQ ID NO: 280          moltype = AA  length = 39
FEATURE                 Location/Qualifiers
REGION                  1..39
                        note = Synthetic construct
source                  1..39
                        mol_type = protein
                        organism = synthetic construct
SEQUENCE: 280
YADSVKGRFT ISRDNAKNTV YLQMNSLKPE DTAVYYCAA                             39

SEQ ID NO: 281          moltype = AA  length = 38
FEATURE                 Location/Qualifiers
REGION                  1..38
                        note = Synthetic construct
source                  1..38
                        mol_type = protein
                        organism = synthetic construct
SEQUENCE: 281
YADSVKGRFT ISRDNAKNTV YLQMNSLKPE DTAVYYCA                              38

SEQ ID NO: 282          moltype = AA  length = 40
FEATURE                 Location/Qualifiers
REGION                  1..40
                        note = Synthetic construct
source                  1..40
                        mol_type = protein
                        organism = synthetic construct
SEQUENCE: 282
YYADSVKGRF TISRDNAKNT VYLQMNSLKP EDTAVYYCAA                            40
```

```
SEQ ID NO: 283         moltype = AA   length = 32
FEATURE                Location/Qualifiers
REGION                 1..32
                       note = Synthetic construct
source                 1..32
                       mol_type = protein
                       organism = synthetic construct
SEQUENCE: 283
RFTISRDNSK NTLYLQMNSL RAEDTAVYYC AK                                   32

SEQ ID NO: 284         moltype = AA   length = 32
FEATURE                Location/Qualifiers
REGION                 1..32
                       note = Synthetic construct
source                 1..32
                       mol_type = protein
                       organism = synthetic construct
SEQUENCE: 284
RFTISRDNAK NTVYLQMNSL KPEDTADYYC AA                                   32

SEQ ID NO: 285         moltype =      length =
SEQUENCE: 285
000

SEQ ID NO: 286         moltype =      length =
SEQUENCE: 286
000

SEQ ID NO: 287         moltype =      length =
SEQUENCE: 287
000

SEQ ID NO: 288         moltype =      length =
SEQUENCE: 288
000

SEQ ID NO: 289         moltype =      length =
SEQUENCE: 289
000

SEQ ID NO: 290         moltype = AA   length = 12
FEATURE                Location/Qualifiers
REGION                 1..12
                       note = Synthetic construct
source                 1..12
                       mol_type = protein
                       organism = synthetic construct
SEQUENCE: 290
YWGQGTQVTV SS                                                         12

SEQ ID NO: 291         moltype = AA   length = 11
FEATURE                Location/Qualifiers
REGION                 1..11
                       note = Synthetic construct
source                 1..11
                       mol_type = protein
                       organism = synthetic construct
SEQUENCE: 291
WGQGTQVTVS S                                                          11

SEQ ID NO: 292         moltype = AA   length = 12
FEATURE                Location/Qualifiers
REGION                 1..12
                       note = Synthetic construct
source                 1..12
                       mol_type = protein
                       organism = synthetic construct
SEQUENCE: 292
VWGPGLLLTV SS                                                         12

SEQ ID NO: 293         moltype = AA   length = 11
FEATURE                Location/Qualifiers
REGION                 1..11
                       note = Synthetic construct
source                 1..11
                       mol_type = protein
                       organism = synthetic construct
SEQUENCE: 293
```

```
                                          -continued

WGPGLLLTVS S                                                                    11

SEQ ID NO: 294           moltype = AA   length = 10
FEATURE                  Location/Qualifiers
REGION                   1..10
                         note = Synthetic construct
source                   1..10
                         mol_type = protein
                         organism = synthetic construct
SEQUENCE: 294
WGQGTLVTVS                                                                      10

SEQ ID NO: 295           moltype = AA   length = 11
FEATURE                  Location/Qualifiers
REGION                   1..11
                         note = Synthetic construct
source                   1..11
                         mol_type = protein
                         organism = synthetic construct
SEQUENCE: 295
WGQGTLVTVS S                                                                    11

SEQ ID NO: 296           moltype = AA   length = 10
FEATURE                  Location/Qualifiers
REGION                   1..10
                         note = Synthetic construct
source                   1..10
                         mol_type = protein
                         organism = synthetic construct
SEQUENCE: 296
WGQGTQVTVS                                                                      10

SEQ ID NO: 297           moltype = AA   length = 11
FEATURE                  Location/Qualifiers
REGION                   1..11
                         note = Synthetic construct
source                   1..11
                         mol_type = protein
                         organism = synthetic construct
SEQUENCE: 297
WGQGTQVTVS S                                                                    11

SEQ ID NO: 298           moltype = AA   length = 12
FEATURE                  Location/Qualifiers
REGION                   1..12
                         note = Synthetic construct
source                   1..12
                         mol_type = protein
                         organism = synthetic construct
SEQUENCE: 298
QWGQGTQVTV SS                                                                   12

SEQ ID NO: 299           moltype = AA   length = 11
FEATURE                  Location/Qualifiers
REGION                   1..11
                         note = Synthetic construct
source                   1..11
                         mol_type = protein
                         organism = synthetic construct
SEQUENCE: 299
YWGQGTQVTV S                                                                    11

SEQ ID NO: 300           moltype = AA   length = 11
FEATURE                  Location/Qualifiers
REGION                   1..11
                         note = Synthetic construct
source                   1..11
                         mol_type = protein
                         organism = synthetic construct
SEQUENCE: 300
WGQGTTVVVS S                                                                    11

SEQ ID NO: 301           moltype = AA   length = 11
FEATURE                  Location/Qualifiers
REGION                   1..11
                         note = Synthetic construct
source                   1..11
                         mol_type = protein
                         organism = synthetic construct
```

```
SEQUENCE: 301
WGKGTQVTVS S                                                            11

SEQ ID NO: 302           moltype =   length =
SEQUENCE: 302
000

SEQ ID NO: 303           moltype =   length =
SEQUENCE: 303
000

SEQ ID NO: 304           moltype =   length =
SEQUENCE: 304
000

SEQ ID NO: 305           moltype =   length =
SEQUENCE: 305
000

SEQ ID NO: 306           moltype =   length =
SEQUENCE: 306
000

SEQ ID NO: 307           moltype =   length =
SEQUENCE: 307
000

SEQ ID NO: 308           moltype =   length =
SEQUENCE: 308
000

SEQ ID NO: 309           moltype =   length =
SEQUENCE: 309
000

SEQ ID NO: 310           moltype =   length =
SEQUENCE: 310
000

SEQ ID NO: 311           moltype = AA   length = 4
FEATURE                  Location/Qualifiers
REGION                   1..4
                         note = Synthetic construct
source                   1..4
                         mol_type = protein
                         organism = synthetic construct
SEQUENCE: 311
GGGS                                                                     4

SEQ ID NO: 312           moltype = AA   length = 4
FEATURE                  Location/Qualifiers
REGION                   1..4
                         note = Synthetic construct
source                   1..4
                         mol_type = protein
                         organism = synthetic construct
SEQUENCE: 312
GGGG                                                                     4

SEQ ID NO: 313           moltype = AA   length = 5
FEATURE                  Location/Qualifiers
REGION                   1..5
                         note = Synthetic construct
source                   1..5
                         mol_type = protein
                         organism = synthetic construct
SEQUENCE: 313
GGGGS                                                                    5

SEQ ID NO: 314           moltype = AA   length = 4
FEATURE                  Location/Qualifiers
REGION                   1..4
                         note = Synthetic construct
source                   1..4
                         mol_type = protein
                         organism = synthetic construct
SEQUENCE: 314
GGSG                                                                     4
```

| | | |
|---|---|---|
| SEQ ID NO: 315<br>FEATURE<br>REGION<br><br>source<br><br><br><br>SEQUENCE: 315<br>GGGGSGGGGS | moltype = AA  length = 10<br>Location/Qualifiers<br>1..10<br>note = Synthetic construct<br>1..10<br>mol_type = protein<br>organism = synthetic construct | 10 |
| SEQ ID NO: 316<br>FEATURE<br>REGION<br><br>source<br><br><br><br>SEQUENCE: 316<br>GGGGSGGGGS GGGGS | moltype = AA  length = 15<br>Location/Qualifiers<br>1..15<br>note = Synthetic construct<br>1..15<br>mol_type = protein<br>organism = synthetic construct | 15 |
| SEQ ID NO: 317<br>FEATURE<br>REGION<br><br>source<br><br><br><br>SEQUENCE: 317<br>GGGGSGGGGS GGGGSGGGGS | moltype = AA  length = 20<br>Location/Qualifiers<br>1..20<br>note = Synthetic construct<br>1..20<br>mol_type = protein<br>organism = synthetic construct | 20 |
| SEQ ID NO: 318<br>FEATURE<br>REGION<br><br>source<br><br><br><br>SEQUENCE: 318<br>GGSGGGSG | moltype = AA  length = 8<br>Location/Qualifiers<br>1..8<br>note = Synthetic construct<br>1..8<br>mol_type = protein<br>organism = synthetic construct | 8 |
| SEQ ID NO: 319<br>FEATURE<br>REGION<br><br>source<br><br><br><br>SEQUENCE: 319<br>GGSGGGSGGG SG | moltype = AA  length = 12<br>Location/Qualifiers<br>1..12<br>note = Synthetic construct<br>1..12<br>mol_type = protein<br>organism = synthetic construct | 12 |
| SEQ ID NO: 320<br>SEQUENCE: 320<br>000 | moltype =   length = | |
| SEQ ID NO: 321<br>SEQUENCE: 321<br>000 | moltype =   length = | |
| SEQ ID NO: 322<br>SEQUENCE: 322<br>000 | moltype =   length = | |
| SEQ ID NO: 323<br>SEQUENCE: 323<br>000 | moltype =   length = | |
| SEQ ID NO: 324<br>SEQUENCE: 324<br>000 | moltype =   length = | |
| SEQ ID NO: 325<br>SEQUENCE: 325<br>000 | moltype =   length = | |
| SEQ ID NO: 326<br>SEQUENCE: 326<br>000 | moltype =   length = | |
| SEQ ID NO: 327 | moltype =   length = | |

| | | |
|---|---|---|
| SEQUENCE: 327 000 | | |
| SEQ ID NO: 328 SEQUENCE: 328 000 | moltype = | length = |
| SEQ ID NO: 329 SEQUENCE: 329 000 | moltype = | length = |
| SEQ ID NO: 330 SEQUENCE: 330 000 | moltype = | length = |
| SEQ ID NO: 331 SEQUENCE: 331 000 | moltype = | length = |
| SEQ ID NO: 332 SEQUENCE: 332 000 | moltype = | length = |
| SEQ ID NO: 333 SEQUENCE: 333 000 | moltype = | length = |
| SEQ ID NO: 334 SEQUENCE: 334 000 | moltype = | length = |
| SEQ ID NO: 335 SEQUENCE: 335 000 | moltype = | length = |
| SEQ ID NO: 336 SEQUENCE: 336 000 | moltype = | length = |
| SEQ ID NO: 337 SEQUENCE: 337 000 | moltype = | length = |
| SEQ ID NO: 338 SEQUENCE: 338 000 | moltype = | length = |
| SEQ ID NO: 339 SEQUENCE: 339 000 | moltype = | length = |
| SEQ ID NO: 340 SEQUENCE: 340 000 | moltype = | length = |
| SEQ ID NO: 341 SEQUENCE: 341 000 | moltype = | length = |
| SEQ ID NO: 342 SEQUENCE: 342 000 | moltype = | length = |
| SEQ ID NO: 343 SEQUENCE: 343 000 | moltype = | length = |
| SEQ ID NO: 344 SEQUENCE: 344 000 | moltype = | length = |
| SEQ ID NO: 345 SEQUENCE: 345 000 | moltype = | length = |
| SEQ ID NO: 346 SEQUENCE: 346 000 | moltype = | length = |

| | | |
|---|---|---|
| SEQ ID NO: 347<br>SEQUENCE: 347 | moltype = | length = 000 |
| SEQ ID NO: 348<br>SEQUENCE: 348 | moltype = | length = 000 |
| SEQ ID NO: 349<br>SEQUENCE: 349 | moltype = | length = 000 |
| SEQ ID NO: 350<br>SEQUENCE: 350 | moltype = | length = 000 |
| SEQ ID NO: 351<br>SEQUENCE: 351 | moltype = | length = 000 |
| SEQ ID NO: 352<br>SEQUENCE: 352 | moltype = | length = 000 |
| SEQ ID NO: 353<br>SEQUENCE: 353 | moltype = | length = 000 |
| SEQ ID NO: 354<br>SEQUENCE: 354 | moltype = | length = 000 |
| SEQ ID NO: 355<br>SEQUENCE: 355 | moltype = | length = 000 |
| SEQ ID NO: 356<br>SEQUENCE: 356 | moltype = | length = 000 |
| SEQ ID NO: 357<br>SEQUENCE: 357 | moltype = | length = 000 |
| SEQ ID NO: 358<br>SEQUENCE: 358 | moltype = | length = 000 |
| SEQ ID NO: 359<br>SEQUENCE: 359 | moltype = | length = 000 |
| SEQ ID NO: 360<br>SEQUENCE: 360 | moltype = | length = 000 |
| SEQ ID NO: 361<br>SEQUENCE: 361 | moltype = | length = 000 |
| SEQ ID NO: 362<br>SEQUENCE: 362 | moltype = | length = 000 |
| SEQ ID NO: 363<br>SEQUENCE: 363 | moltype = | length = 000 |
| SEQ ID NO: 364<br>SEQUENCE: 364 | moltype = | length = 000 |
| SEQ ID NO: 365<br>SEQUENCE: 365 | moltype = | length = 000 |
| SEQ ID NO: 366<br>SEQUENCE: 366 | moltype = | length = 000 |

-continued

SEQ ID NO: 367    moltype =    length =
SEQUENCE: 367
000

SEQ ID NO: 368    moltype =    length =
SEQUENCE: 368
000

SEQ ID NO: 369    moltype =    length =
SEQUENCE: 369
000

SEQ ID NO: 370    moltype =    length =
SEQUENCE: 370
000

SEQ ID NO: 371    moltype =    length =
SEQUENCE: 371
000

SEQ ID NO: 372    moltype =    length =
SEQUENCE: 372
000

SEQ ID NO: 373    moltype =    length =
SEQUENCE: 373
000

SEQ ID NO: 374    moltype =    length =
SEQUENCE: 374
000

SEQ ID NO: 375    moltype =    length =
SEQUENCE: 375
000

SEQ ID NO: 376    moltype =    length =
SEQUENCE: 376
000

SEQ ID NO: 377    moltype =    length =
SEQUENCE: 377
000

SEQ ID NO: 378    moltype =    length =
SEQUENCE: 378
000

SEQ ID NO: 379    moltype =    length =
SEQUENCE: 379
000

SEQ ID NO: 380    moltype =    length =
SEQUENCE: 380
000

SEQ ID NO: 381    moltype =    length =
SEQUENCE: 381
000

SEQ ID NO: 382    moltype =    length =
SEQUENCE: 382
000

SEQ ID NO: 383    moltype =    length =
SEQUENCE: 383
000

SEQ ID NO: 384    moltype =    length =
SEQUENCE: 384
000

SEQ ID NO: 385    moltype =    length =
SEQUENCE: 385
000

SEQ ID NO: 386    moltype =    length =
SEQUENCE: 386

| | | |
|---|---|---|
| SEQ ID NO: 387 SEQUENCE: 387 000 | moltype = length = | |
| SEQ ID NO: 388 SEQUENCE: 388 000 | moltype = length = | |
| SEQ ID NO: 389 SEQUENCE: 389 000 | moltype = length = | |
| SEQ ID NO: 390 SEQUENCE: 390 000 | moltype = length = | |
| SEQ ID NO: 391 SEQUENCE: 391 000 | moltype = length = | |
| SEQ ID NO: 392 SEQUENCE: 392 000 | moltype = length = | |
| SEQ ID NO: 393 SEQUENCE: 393 000 | moltype = length = | |
| SEQ ID NO: 394 SEQUENCE: 394 000 | moltype = length = | |
| SEQ ID NO: 395 SEQUENCE: 395 000 | moltype = length = | |
| SEQ ID NO: 396 SEQUENCE: 396 000 | moltype = length = | |
| SEQ ID NO: 397 SEQUENCE: 397 000 | moltype = length = | |
| SEQ ID NO: 398 SEQUENCE: 398 000 | moltype = length = | |
| SEQ ID NO: 399 SEQUENCE: 399 000 | moltype = length = | |
| SEQ ID NO: 400 SEQUENCE: 400 000 | moltype = length = | |
| SEQ ID NO: 401 FEATURE REGION source | moltype = AA  length = 10 Location/Qualifiers 1..10 note = Synthetic 1..10 mol_type = protein organism = synthetic construct | |
| SEQUENCE: 401 EPKSCDKTHT | | 10 |
| SEQ ID NO: 402 FEATURE REGION source | moltype = AA  length = 4 Location/Qualifiers 1..4 note = Synthetic 1..4 mol_type = protein organism = synthetic construct | |
| SEQUENCE: 402 CPPC | | 4 |
| SEQ ID NO: 403 | moltype = AA  length = 9 | |

```
FEATURE                 Location/Qualifiers
REGION                  1..9
                        note = Synthetic
source                  1..9
                        mol_type = protein
                        organism = synthetic construct
SEQUENCE: 403
PAPELLGGP                                                                9

SEQ ID NO: 404          moltype = AA  length = 209
FEATURE                 Location/Qualifiers
REGION                  1..209
                        note = Synthetic
source                  1..209
                        mol_type = protein
                        organism = synthetic construct
SEQUENCE: 404
SVFLFPPKPK DTLMISRTPE VTCVVVDVSH EDPEVKFNWY VDGVEVHNAK TKPREEQYNS          60
TYRVVSVLTV LHQDWLNGKE YKCKVSNKAL PAPIEKTISK AKGQPREPQV YTLPPSRDEL         120
TKNQVSLTCL VKGFYPSDIA VEWESNGQPE NNYKTTPPVL DSDGSFFLYS KLTVDKSRWQ         180
QGNVFSCSVM HEALHNHYTQ KSLSLSPGK                                          209

SEQ ID NO: 405          moltype = AA  length = 26
FEATURE                 Location/Qualifiers
REGION                  1..26
                        note = Synthetic
source                  1..26
                        mol_type = protein
                        organism = synthetic construct
SEQUENCE: 405
EVQLQASGGG FVQPGGSLRL SCAASG                                              26

SEQ ID NO: 406          moltype = AA  length = 19
FEATURE                 Location/Qualifiers
REGION                  1..19
                        note = Synthetic
source                  1..19
                        mol_type = protein
                        organism = synthetic construct
SEQUENCE: 406
MGWFRQAPGK EREFVSAIS                                                      19

SEQ ID NO: 407          moltype = AA  length = 38
FEATURE                 Location/Qualifiers
REGION                  1..38
                        note = Synthetic
source                  1..38
                        mol_type = protein
                        organism = synthetic construct
SEQUENCE: 407
YADSVKGRFT ISRDNSKNTV YLQMNSLRAE DTATYYCA                                 38

SEQ ID NO: 408          moltype = AA  length = 12
FEATURE                 Location/Qualifiers
REGION                  1..12
                        note = Synthetic
source                  1..12
                        mol_type = protein
                        organism = synthetic construct
SEQUENCE: 408
YWGQGTQVTV SS                                                             12

SEQ ID NO: 409          moltype = AA  length = 355
FEATURE                 Location/Qualifiers
source                  1..355
                        mol_type = protein
                        organism = synthetic construct
SEQUENCE: 409
EVQLQASGGG FVQPGGSLRL SCAASGTFDQ RSRMGWFRQA PGKEREFVSA ISSWSDGSRK          60
YADSVKGRFT ISRDNSKNTV YLQMNSLRAE DTATYYCAAF FADAYTIPFY YWGQGTQVTV         120
SSAEPKSCDK THTCPPCPAP ELLGGPSVFL FPPKPKDTLM ISRTPEVTCV VVDVSHEDPE         180
VKFNWYVDGV EVHNAKTKPR EEQYNSTYRV VSVLTVLHQD WLNGKEYKCK VSNKALPAPI         240
EKTISKAKGQ PREPQVYTLP PSRDELTKNQ VSLTCLVKGF YPSDIAVEWE SNGQPENNYK         300
TTPPVLDSDG SFFLYSKLTV DKSRWQQGNV FSCSVMHEAL HNHYTQKSLS LSPGK              355
```

BRAIN-TARGETING SINGLE DOMAIN ANTIBODIES AND PURIFICATION METHODS

STATEMENT OF GOVERNMENT INTEREST

This invention was made with Government support under Contract No. DE-NA0003525 awarded by the United States Department of Energy/National Nuclear Security Administration. The U.S. Government has certain rights in the invention

REFERENCE TO A SEQUENCE LISTING APPENDIX

A sequence listing appendix including an ASCII formatted file accompanies this application. The appendix includes a file named "SD-15931.xml," created on Aug. 29, 2022 (size of 274 kilobytes), which is hereby incorporated by reference in its entirety.

FIELD

The present disclosure relates to single domain antibodies (sdAbs) or the variable target binding domain of a heavy chain only antibody. In particular, the sdAbs disclosed herein are configured to target and traverse the blood brain barrier to access the central nervous system.

BACKGROUND

Therapeutic agents for various internal diseases are conventionally applied to the body systemically, either through oral consumption, inhalation, mucosal absorption, or radiation therapy. These therapies are applied to the whole body or a broad area, and thus, pose risks to the whole body or broad area, or at a minimum are significantly diluted as they proceed throughout the bloodstream or area of a patient. For example, anti-cancer chemotherapy provides a cancer killing agent that attacks harmful cancer cells, but is also harmful to other cells in the body. Radiation is harmful to the body as a whole, even though it is targeted to a particular location where the cancer resides. Targeted therapeutics, i.e., agents that are delivered directly to a particular tissue or organ, are advantageous in eliminating or decreasing unwanted side-effects to the rest of the body, because more of the dosage can be delivered directly to the area of infection or concern. In such therapeutic systems lower overall dosage amounts can be used since they are more efficiently delivered to the problem area. Also, with targeted therapeutics, barriers obstructing therapeutic efficacy are bypassed, such as poor gastrointestinal absorption and first-pass metabolism of pharmaceuticals or other therapeutic agents in the liver.

The brain would be a desirable target to deliver pharmaceuticals or other beneficial cargo to address infections, malignancies, or degenerative conditions. However, the blood brain barrier is notoriously difficult to reliably permeate with beneficial results. This is due to blood vessels in the brain that vascularize the central nervous system and have unique properties to tightly regulate the movement of ions, molecules, and cells between the blood and the brain. Much effort has been put into strategies to provide drug delivery that will pass the blood brain barrier. See Larsen J M, Martin D R, Byrne M E., "Recent advances in delivery through the blood-brain barrier," *Curr Top Med Chem* 14: 1148-1160 (2014).

Current methods of delivery across the blood brain barrier include receptor mediated transcytosis (RMT). Only a subset of receptors have been explored and little to no improvement has been made in penetration of the blood brain barrier in over 10 years. Current targets (insulin and transferrin receptor) identified in vitro, lack physiological context and in vivo effectiveness, with delivery of less than 5%. Thus, there is long felt and unresolved need for effective delivery mechanisms to reach across the blood brain barrier.

SUMMARY

Disclosed herein are sdAbs configured for crossing the blood-brain barrier in a human or mammal brain. Methods of using such sdAbs are also described herein, such as methods of RMT mediated transport through blood-brain barrier (BBB) endothelial cells, fusion with other sdAbs and heavy chain only antibodies with beneficial functionalities as a BBB shuttle, transporting biochemical or pharmaceutical species with beneficial functionalities, and treating, prophylactically treating, or diagnosing a disease, condition, or malignancy.

SdAbs, as disclosed herein, are the antigen binding region of heavy chain only antibodies first identified in camels. These sdAbs described here are synthetic humanized sdAbs developed based on a library as described below. SdAbs can also be produced as heavy chain only antibodies which are smaller and more modular than conventional antibodies with the ability to engage the immune response. SdAbs disclosed herein may be formulated to include the Fc region to generate heavy chain only antibodies (hcAbs).

The sdAbs or sdAb constructs disclosed herein are effective as sdAbs and as heavy-chain only modified antibodies that are configured to penetrate the BBB endothelium of the human or mammal brain. The brain targeting sdAbs may also be referred to herein as "shuttles," which indicates their capacity for targeting a desired end-point and for carrying a therapeutic cargo.

It has been demonstrated that once the protein sequence, or genetic coding, of a virus has been identified, a sdAb-based countermeasure can be developed within 120 days. Speeding up the discovery of neutralizing antibodies could reduce the impact and spread of future viral outbreaks. Neutralizing heavy chain only antibodies and sdAbs represent an attractive strategy due to their modular nature, capability to be deployed in multivalent sdAb combinations, and their corresponding ability to work effectively against families of viruses and emerging variants. Importantly, utilizing heavy chain only antibodies further allows exploitation of distinct immune pathways specifically linked to a given virus or family of viruses. Thus, sdAb treatments can be selected to therapeutically target commonalities between viral family members and their variants, but also can be rapidly adapted to additional disparate variants as they emerge.

Modular sdAbs can be combined with other sdAbs to increase their ability to bind to the virus or target specific tissues. The bispecific nature of combining sdAbs can increase therapeutic efficacy by clearing the infection locally, and reducing the likelihood of systemic complications.

Additionally, due to the small size of the sdAbs, they can be released into the blood and penetrate tissues more thoroughly than conventional antibodies. SdAb therapies can also target an infection site directly, decreasing the dose needed and increasing efficacy. SdAbs can also be administered via aerosol, so they can be given to a patient orally or in an inhalable form. Conventional antibody treatments are less versatile.

These qualities and features of sdAbs make tissue-targeted sdAb therapies potentially much more effective than current solutions. These treatments are also easier and cheaper to manufacture.

In particular, provided herein are brain-tissue targeting sdAb-based constructs comprising a shuttle sdAb and a biochemical, diagnostic, or pharmaceutical cargo. In an embodiment, a brain-tissue targeting shuttle sdAb construct comprises: a sdAb and an Fc domain and hinge region of human IgG1 protein. The sdAb is coupled to the hinge region of the Fc domain. The sdAb construct is configured to bind to a receptor on the BBB endothelium, triggering RMT transport across the BBB. While it was not conclusively, experimentally determined that "binding" under some definitions of that term technically took place between the sdAb and an epitope on the brain tissue, it was indicated that specific enrichment of the sdAbs was found in the brain tissue and that was not found at all or to the same extent in other tissues (e.g., 10% or greater accumulation in the brain than, for example, the liver). The term "targeting" contemplates an affinity for binding to or some other mechanism of coupling to the tissue.

In some aspects, the techniques described herein relate to a sdAb construct, including a first sdAb with a binding domain, wherein the binding domain includes: a first complementarity determining region including a polypeptide sequence having at least 80% sequence identity to any one of SEQ ID NOs: 1-25; a second complementarity determining region including a polypeptide sequence having at least 80% sequence identity to any one of SEQ ID NOs: 26-50; and a third complementarity determining region including a polypeptide sequence having at least 80% sequence identity to any one of SEQ ID NOs: 51-75.

In some aspects, the techniques described herein relate to a vector including: a phage configured to express a first sdAb with a binding domain, wherein the binding domain includes: a first complementarity determining region including a polypeptide sequence having at least 80% sequence identity to any one of SEQ ID NOs: 1-25; a second complementarity determining region including a polypeptide sequence having at least 80% sequence identity to any one of SEQ ID NOs: 26-50; and a third complementarity determining region including a polypeptide sequence having at least 80% sequence identity to any one of SEQ ID NOs: 51-75.

In some aspects, the techniques described herein relate to a method for treating, diagnosing, or prophylactically treating a disease, condition, or malignancy including: administering a pharmaceutically acceptable composition including an isolated or purified sdAb construct to a patient in need thereof; wherein the sdAb construct includes a sdAb including: a first complementarity determining region including a polypeptide sequence having at least 80% sequence identity to any one of SEQ ID NOs: 1-25; a second complementarity determining region including a polypeptide sequence having at least 80% sequence identity to any one of SEQ ID NOs: 26-50; and a third complementarity determining region including a polypeptide sequence having at least 80% sequence identity to any one of SEQ ID NOs: 51-75; and a cargo.

In embodiments of the binding domain, the first framework region includes a polypeptide sequence having at least 90% sequence identity to any one of SEQ ID NOs: 190-212 or 405. In embodiments, the second framework region includes a polypeptide sequence having at least 90% sequence identity to any one of SEQ ID NOs: 220-243 or 406. In embodiments, the third framework region includes a polypeptide sequence having at least 90% sequence identity to any one of SEQ ID NOs: 250-284 or 407. In embodiments, the fourth framework region includes a polypeptide sequence having at least 90% sequence identity to any one of SEQ ID NOs: 290-301 or 408.

In an embodiment, the antibody or fragment thereof further includes a linker disposed between the first and second binding domains. Non-limiting linkers include any described herein, such as GGG and SEQ ID NOs: 311-319 and/or A.

In an embodiment, the method includes: administering an isolated or purified antibody or fragment thereof (e.g., any described herein) to a subject in need thereof. In other embodiments, the isolated or purified antibody or fragment thereof is provided as a pharmaceutical composition comprising a shuttle sdAb for a biochemical or pharmaceutically active agent.

In an embodiment, the viral infection includes an infection from an alpha virus, for example, an encephalitic alpha virus.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "*Molecular Cloning: A Laboratory Manual*," Second Edition, Cold Spring Harbor Laboratory Press, Cold Spring Harbor (1989), particularly Chapter 11 and Table 11.1 therein; and Sambrook J and Russell W, "*Molecular Cloning: A Laboratory Manual*," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "fragment" means a portion of a nucleic acid or a polypeptide that is at least one nucleotide or one amino acid shorter than the reference sequence. This portion contains, preferably, at least about 85%, 95%, or 99% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 80%, about 90%, about 95%, about 97%, about 98%, about 99%, or about 100%) identical to any of the sequences described herein. In certain embodiments, a polypeptide disclosed herein includes 2, 3, 4, 5, 6, 7, 8, 9, 10, or more mutations (e.g., one or more conservative amino acid substitutions, as described herein). In yet another example, any nucleic acid fragment can include a stretch of at least about 5 about 10, about 28, about 30, or more nucleotides that are at least about 80%, about 90%, about 95%, about 87%, about 98%, about 99%, or about 100% identical to any of the sequences described herein.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M).

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined within the skill in the art, for instance, by the BLAST (Basic Local Alignment Search Tool; Altschul S F et al., *J. Mol. Biol.* 1990; 215:403-10). This algorithm is accessible using publicly available computer software such as "Best Fit" (Smith T F et al., *Adv. Appl. Math.* 1981; 2(4):482-9) as incorporated into GeneMatcher Plus TM. In addition, those skilled in the art can determine appropriate parameters for measuring alignment, including any algorithms needed to achieve optimal alignment over the length of the sequences being compared. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an antiviral agent, an effective amount of an agent is, for example, an amount sufficient to achieve a reduction in viral load or a mitigation of a symptom related to a viral infection or a delay in a symptom related to a viral infection, as compared to the response obtained without administration of the agent.

By "subject" or "patient" is meant a human or non-human animal (e.g., a mammal).

By "treating" a disease, malignancy, or condition in a subject is meant reducing at least one symptom of the disease, malignancy, or condition by administrating a therapeutic agent to the subject. By "treating prophylactically" or "prophylactically treating" a disease, malignancy, or condition in a subject is meant reducing the frequency of occurrence of or reducing the severity of a disease, malignancy or condition by administering a therapeutic agent to the subject prior to the onset of disease symptoms. Beneficial or desired results can include, but are not limited to, alleviation or amelioration of one or more symptoms or conditions; diminishment of extent of disease, malignancy, or condition; stabilized (i.e., not worsening) state of disease, malignancy, or condition; preventing spread of disease, malignancy, or condition; delay or slowing the progress of the disease, malignancy, or condition; amelioration or palliation of the disease, malignancy, or condition; and/or remission (whether partial or total), whether detectable or undetectable.

By "attached," "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

By "linker" is meant any useful multivalent (e.g., bivalent) component useful for joining to different portions or segments. Exemplary linkers include a nucleic acid sequence, a chemical linker, etc. In one instance, the linker of the guiding component (e.g., linker L in the interacting portion of the guiding component) can have a length of from about 3 nucleotides to about 100 nucleotides. For example, the linker can have a length of from about 3 nucleotides (nt) to about 90 nt, from about 5 nucleotides (nt) to about 80 nt, from about 6 nucleotides (nt) to about 70 nt, from about 8 nucleotides (nt) to about 50 nt, from about 10 nucleotides (nt) to about 350 nt.

The term "sdAb construct" as used herein means one or more sdAbs coupled to another structure, such as, a portion of an antibody, a modified antibody, a synthetic or natural particle, a humanized Fc, a mammalian Fc or other Fc, or another sdAb these may include or may additionally be coupled to other structures such as linkers or hinge regions.

BRIEF DESCRIPTION OF THE DRAWINGS

FIG. 3 provides example sequences for CDRs, including sequences for complementarity determining region 1 (CDR1, SEQ ID NOs: 1-25), complementarity determining region 2 (CDR2, SEQ ID NOs: 26-50), and complementarity determining region 3 (CDR3, SEQ ID NOs: 51-75).

FIG. 4 is an example schematic of an antibody having framework regions (FRs) interspersed with complementarity determining regions (CDRs), in which a sdAb can include framework regions 1–4 (FR1, FR2, FR3, and FR4) with interspersed CDR1, CDR2, and CDR3.

FIG. 5 provides example sdAb sequences corresponding to SEQ ID NOs: 76-90.

FIG. 6 provides example sdAb sequences corresponding to SEQ ID NOs: 91-100.

FIG. 8 is a schematic showing an example of the isoelectric precipitation and endotoxin purification steps.

FIG. 9 is a table showing phage titers at certain steps in the example methods disclosed herein.

FIG. 10 is a schematic showing the cfu counts at different rounds of the biopanning disclosed in the Examples.

FIG. 11 is a table showing enrichment factors for various sequences in the second and third rounds of biopanning disclosed in the Examples.

FIG. 14 lists sequences for framework regions FR1, FR2, FR3, and FR4 (SEQ ID NOs. 405-408, respectively).

FIG. 15 provides additional example sequences for framework regions FR1, FR2, FR3, and FR4.

FIGS. 16A-16D provide (A) a sequence alignment of example FR1 sequences (SEQ ID NOs:190-212); (B) a sequence alignment of example FR2 sequences (SEQ ID NOs:220-243); (C) a sequence alignment of example FR3 sequences (SEQ ID NOs:250-284); and (D) a sequence alignment of example FR4 sequences (SEQ ID NOs:290-301).

DETAILED DESCRIPTION

This disclosure relates to an isolated or purified sdAb construct comprising a sdAb with a binding region that binds to human or mammalian receptors of the BBB endothelium. In an embodiment, the brain-targeting sdAbs are bound to a humanized Fc and/or the sdAb construct includes a biochemical or pharmaceutical active agent.

From a novel synthetic library that was designed to find highly potent sdAbs that are both easier to manufacture and more accessible to certain proteins and smaller tissues than conventional antibodies, the sdAbs disclosed herein were identified and tested. Certain sdAbs were paired together on a humanized Fc and tested and found to be present in sufficient quantities to indicate effective targeting of and delivery to brain tissue.

Previous libraries for screening in vivo involved only using short peptides or smaller libraries with less diversity (1/10 the size of the library disclosed herein. Only recently has DNA synthesis technology enabled libraries of this size to be produced. Challenges involved transforming enough bacteria to get enough diversity, and 150 transformations on 8 square meters of plating (greater than 1000 plates) were utilized to overcome this.

As disclosed herein, complementarity determining regions (CDRs) were identified that provide enhanced efficacy in targeting brain tissue, as determined by in vivo testing. Such CDRs can be provided in an antibody having a useful format, such as a sdAb, either separate or joined to a human Fc and/or joined to a useful cargo or other forms described herein.

Figure 1:
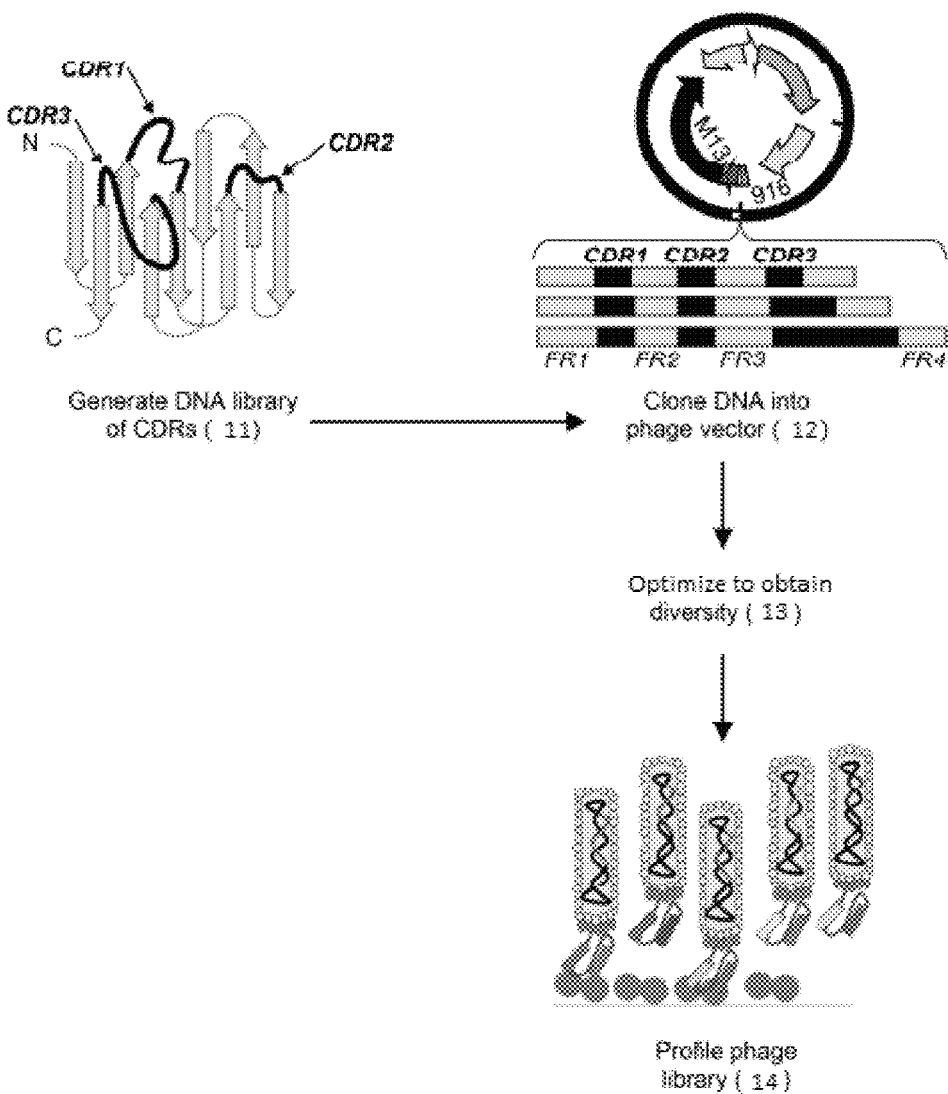
FIG. 1 shows a schematic of an example method for synthesizing a library of sdAbs.
Figure 2:
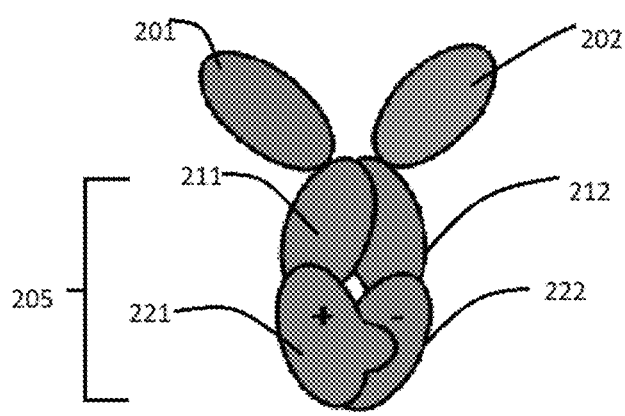
FIG. 2 is a schematic of an example sdAb construct.

CDRs for the sdAb were identified starting with using a phage library (FIG. 1). FIG. 1 shows a description of how the library was constructed. The library incorporated both the diversity and prevalence of amino acids at key positions in each of the CDR1 and CDR2 derived from a single domain antibody (sdAb) database. This database contained sequences of validated sdAbs or sdAbs from both synthetic and natural sources from both naïve and immune repertoires. Components of the database were curated using sequences derived from existing databases (Protein Data Bank and NCBI) and publications.

Such a library can be constructed by generating 101 a DNA library of CDRs with high diversity, cloning 102 the DNA into a phage vector to express sdAbs as fusion proteins with the phage coat protein, optimizing 103 the transformation to obtain phages having sufficient diversity, and profiling 104 the phage library by sequencing. Diversity can include distribution in both the amino acid content and the length of the CDRs.

The library used herein was designed to have 3 different CDR3 lengths and incorporated the natural prevalence of amino acid at specific CDR positions for CDR1 and CDR2 derived from 655 effective sdAbs selected with information provided in Emily E. Wilton, et al., "sdAb-DB: The Single Domain Antibody Database," *ACS Synthetic Biology* 2018 7 (11), 2480-2484, DOI: 10.1021/acssynbio.8b00407, incorporated herein by reference. Wilton et al, recite that with respect to the sdAb-db, "Although the hcAbs of camelids and sharks differ somewhat in structure, their single N-terminal domain (VHH and VNAR, respectively) contain the ability to bind an antigen without domain pairing using three complementarity-determining regions (CDRs) . . . . These N-terminal domains have been named single domain antibodies (sdAbs) or nanobodies and have become promising tools for life scientists, protein engineers and synthetic biologists alike" (p. 2480).

For CDR3 all amino acids were used with the exception of cysteine and methionine. The library was constructed using novel DNA synthesis technology ensuring high quality and full length sdAbs with low incidence of stop codons. These attributes allow for the identification of highly potent binders to desired targets with femtomolar to nanomolar dissociation constants. The library was cloned into the pADL20c M13 phagemid vector, which allowed expression of sdAbs as a fusion protein to coat protein gIIIp of M13 phage. Purification and concentration steps were also taken to improve the library sample for in vivo testing.

The purified and concentrated library was then screened by intravenous injection into five mice. The mice brains were harvested one-hour later. The brains were dissociated, phage extracted, grown up, re-purified, and brain-targeting sdAb producing phages were re-injected into five mice two additional times (as described herein) to ensure brain-targeting sdAb enrichment in the brain above other tissues.

Phage populations at each round were sequenced to gauge enrichment and selection over time. The several consecutive rounds of screening in vivo resulted in the enrichment of several sdAbs with a high degree of sequence similarity and clustering. From this in vivo biopanning campaign 25 top candidate sdAbs for minimally-invasive brain-targeting countermeasures were identified.

Further information on the library is disclosed in the Examples section and in the publication Stefan M A, Light Y K, Schwedler J L, McIlroy P R, Courtney C M, Saada E A, Thatcher C E, Phillips A M, Bourguet F A, Mageeney C M, McCloy S A, Collette N M, Negrete O A, Schoeniger J S, Weilhammer D R, Harmon B. *Development of potent and effective synthetic SARS-Cov-2 neutralizing nanobodies*. MAbs. 2021 January-December; 13(1):1958663 (published online Aug. 4, 2021) incorporated herein by reference. In particular, plasmids for expression of the sdAb construct comprising the sdAbs and a humanized Fc region (Nb-huFc) were produced as described in Stefan M A, et al.

The CDRs identified in the screening process can be provided in the form of an antibody. The antibody can have a useful form, such as one or more of the following domains: a single variable domain (VHH) or sdAb, a variable heavy domain (VH), a variable light domain (VL), a single-chain variable-fragment (scFv) antibody, a monoclonal antibody (mAb), an antigen-binding fragment (Fab), a fragment crystallizable region (Fc region), a heavy-chain only antibody (HcAb), an Immunoglobulin G (IgG) antibody, as well as bivalent, trivalent, tetravalent, multivalent, biparatropic, bispecific, multispecific chimeric, and humanized forms thereof. Any of the forms can include a linker between a first amino acid sequence (any domain herein, e.g., such as VH) and a second amino acid sequence (any domain herein, e.g. such as VL). In some embodiments, the sdAb has a molecular weight of 10 to 20 kDa, such as, e.g., 12 to 16 kDa, or 14 kDa to 15 kDa.

The sdAb construct includes a plurality of VHH domains, in which each VHH domain is different. Furthermore, each VHH domain can bind to the same target, the same portion of the same target, different targets, or different portions of the same target. Non-limiting targets are described herein.

FIG. 2 is a simplified illustration of an example sdAb construct in the form of a modified antibody. The sdAb construct comprises a first sdAb 201 and second sdAb 202. Each of the first and second sdAbs comprise first and second binding regions, or first and second paratopes. The sdAbs are heavy chains (VHH domains) that are coupled to a useful amino acid sequence, such as a Fc domain 205, e.g., a humanized Fc domain. The Fc domain, as shown, includes CH2 (211, 212) and CH3 (221, 222) domains. The VHH domains can be fused to other humanized forms of constant domains, such as Fc, CH1, CH2, CH3, and CL domains. Such VHH domains can also be fused to other forms, such as IgG1, IgG3, IgA, or IgM.

Yet other forms can include an Fc region and a Fab; or an Fc region and a VHH. The Fc region can include heavy chains present in any useful isotype (A, E, G, or M), such as Immunoglobulin G (e.g., IgG1, IgG2a, or IgG3). The Fab region can include domains from the heavy chains, including the variable heavy (VH) domains. Within the VH domain, CDRs can be configured to bind to a target of interest. The VHH domain can include CDRs configured to bind to a target of interest.

The first and second sdAbs can be the same or different. In an embodiment, the first sdAb is configured to cross the BBB by RMT and the second sdAb is configured to act as a pharmaceutically or biochemically active agent. In an embodiment, both sdAbs are configured to cross the BBB by RMT(while still being the same or different) and another portion of the sdAb construct is configured to couple to a biochemical or pharmaceutically active cargo through linkage to the Fc domain.

The Fc region of the constructs herein can include a native immunoglobulin, i.e., as formed by the dimeric association of the respective Fc domains (or Fc moieties) of its two heavy chains, in which a native Fc region is homodimeric and comprises two polypeptide chains; or a genetically-fused Fc region or a single-chain Fc region (scFc region), in which a synthetic dimeric Fc region comprised of Fc domains (or Fc moieties) are genetically linked within a single polypeptide chain (i.e., encoded in a single contiguous genetic sequence) as described. In one embodiment, the construct includes a complete Fc region, whether present as one polypeptide chain (an scFc molecule) or in the wild-type form as two polypeptide chains.

The Fc region can include a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

In an embodiment, the Fc region includes an upper hinge, a core, and a lower hinge, connected in that order. The upper hinge is connected to the FR4 region of the sdAb and the lower hinge is connected to the human Fc region. These components may have the following sequences presented in Table 1, or a sequence having at least 90% sequence identity, such as at least 95%, or at least 98% sequence identity. In an exemplary embodiment, a sdAb coupled to a human Fc region is in accordance with SEQ ID NO: 406. In SEQ ID No: 406, the upper hinge corresponds to SEQ ID No: 401, the core is SEQ ID NO: 402, the lower hinge corresponds to SEQ ID No: 403, and the mutated human Fc region is SEQ ID No: 405 (see FIG. 14). SEQ ID. No: 404 is non-mutated human Fc region. SEQ ID NO: 409 is an example sequence of a full sdAb plus Fc region with A as a linker between the fourth FR and the upper hinge. All SEQ ID NOS: 76-100 included A as a linker to the Fc region as tested in the Example below. In SEQ ID NO: 409 the Fc region is underlined, the A linker is bolded and underlined, and the CDRs are bolded.

TABLE 1

| Description | SEQ ID NO: | Sequence |
|---|---|---|
| Upper Hinge | 401 | EPKSCDKTHT |
| Core | 402 | CPPC |
| Lower Hinge | 403 | PAPELLGGP |
| Human Fc Region | 404 | SVFLFPPKPKDTLMISRTPEVTCVVVDVSHE DPEVKFNWYVDGVEVHNAKTKPREEQYNSTY RVVSVLTVLHQDWLNGKEYKCKVSNKALPAP IEKTISKAKGQPREPQVYTLPPSRDELTKNQ VSLTCLVKGFYPSDIAVEWESNGQPENNYKT TPPVLDSDGSFFLYSKLTVDKSRWQQGNVFS CSVMHEALHNHYTQKSLSLSPGK |
| Example SdAb coupled to human Fc Region | 409 | EVQLQASGGGFVQPGGSLRLSCAASGTFDQR SRMGWFRQAPGKEREFVSAISSWSDGSRKYA DSVKGRFTISRDNSKNTVYLQMNSLRAEDTA TYYCAAFFADAYTIPFYYWGQGTQVTVSSA<u>A</u> <u>PKSCDKTHTCPPCPAPELLGGPSVFLFPPKP KDTLMISRTPEVTCVVVDVSHEDPEVKFNWY VDGVEVHNAKTKPREEQYNSTYRVVSVLTVL</u> |

TABLE 1-continued

| Description | SEQ ID NO: | Sequence |
|---|---|---|
| | | <u>HQDWLNGKEYKCKVSNKALPAPIEKTISKAK GQPREPQVYTLPPSRDELTKNQVSLTCLVKG FYPSDIAVEWESNGQPENNYKTTPPVLDSDG SFFLYSKLTVDKSRWQQGNVFSCSVMHEALH NHYTQKSLSLSPGK</u> |

The Fc domains or moieties of a polypeptide may be from any isotype (A, E, G, or M) and may be derived from different immunoglobulin molecules. For example, an Fc domain or moiety of a polypeptide may comprise a CH2 and/or CH3 domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

The constructs herein can be modified antibodies, which includes synthetic forms of antibodies that are altered such that they are not naturally occurring, e.g., antibodies that comprise at least two heavy chain portions but not two complete heavy chains (such as, domain deleted antibodies or minibodies); engineered antibodies having synthetic linkers, such as any described herein; and multispecific forms of antibodies (e.g., bispecific, trispecific, etc., forms of any antibody, such as a sdAb) altered to bind to two or more different antigens, e.g., to a virus, such as a coronavirus and another therapeutically relevant target binding site, e.g., a brain cell tissue.

Modified antibodies can include other types of modifications, such as chemical modification (e.g., pegylation, glycosylation, lipidation, etc.), attachment to a particle or liposome, or bonding to a protein (e.g., a serum protein, a cytokine) or a cell (e.g., a CAR-T cell).

The constructs herein can be "chimeric" or "fusion" proteins. Such proteins comprise a first amino acid sequence linked to a second amino acid sequence to which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created using methods well known in the art, for example, by chemical synthesis, or by creating and translating a polynucleotide in which the peptide regions are encoded in the desired relationship.

Such forms or fusions can include a linker disposed between any number of domains, in which non-limiting linkers are described herein. Any useful linker can be employed, such as a peptide linker that can be cleavable or non-cleavable. Linkers can include or consist of a sequence according to the formula $[(Gly)_m(Ser)]_n(Gly)_p$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. Alternatively, the linker sequence includes or consists of a sequence according to the formula $(Gly)_p[(Ser)(Gly)_m]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. In another embodiment, the linker sequence includes or consists of a sequence according to the formula [(Gly)$_m$(Ser)(Gly)$_p$]$_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. In an embodiment, a linker between the brain-targeting sdAb (e.g., FR4) and an upper hinge region is alanine (A). Further non-limiting linkers include any described herein, such as in GGG and SEQ ID NOs: 311-319 (Table 2).

TABLE 2

Example linkers

| Name | Sequence | SEQ ID NO: |
|---|---|---|
| G$_3$ | GGG | |
| G$_3$S | GGGS | 311 |
| G$_4$ | GGGG | 312 |
| G$_4$S | GGGGS | 313 |
| G$_2$SG | GGSG | 314 |
| (G$_4$S)$_2$ | GGGGSGGGGS | 315 |
| (G$_4$S)$_3$ | GGGGSGGGGSGGGGS | 316 |
| (G$_4$S)$_4$ | GGGGSGGGGSGGGGSGGGGS | 317 |
| (G$_2$SG)$_2$ | GGSGGGSG | 318 |
| (G$_2$SG)$_3$ | GGSGGGSGGGSG | 319 |

The constructs can include other variations. Such variations can include one or more amino acids that facilitate humanization of an initial sequence. Humanization can include use of one or more amino acids present in a human form of the constant or variable regions (e.g., frameworks regions or CDRs). In other embodiments, the variation can include a sequence that lacks Cys and Met residues. In yet other embodiments, the CDR can have an altered length, such as a length from about 4-9 amino acids, 9-12 amino acids, or 12-15 amino acids.

In an embodiment, the sdAb construct can bind a target (e.g., any described herein or any RMT receptor), in which such binding can be characterized by analysis of brain tissue samples in mice. In an embodiment, the sdAb construct can bind a target (e.g., any described herein, such as an endothelial cell) and be characterized by histology, florescence microscopy, or ELISA. In an embodiment, a sdAb disclosed herein has a molecular weight of 20 kDa to 10 kDa, such as 16 kDa to 12 kDa, or 15 kDa to 11 kDa. Through the library screening process and testing disclosed herein, 25 sdAbs with affinity for targeting the brain were identified.

In one embodiment, the brain targeting sdAb includes or is a polypeptide sequence having at least 90% sequence identity to any one of SEQ ID NOs: 76-100, such as at least 95%, or at least 98% sequence identity).

The sequence identity percent, as that term is used herein, includes fragments within the given identity percent. Examples of fragments can include a polypeptide that is, e.g., one amino acid shorter than the reference CDR sequence selected from SEQ ID NOs: 1-75. In an embodiment, the omitted amino acid can be removed from the C-terminus. This omission of others can also be covered as an absent amino acid under a percent sequence identity calculation.

In an embodiment, a sdAb construct comprises a first binding domain, wherein the first binding domain comprises: a first complementarity determining region comprising a polypeptide sequence having at least 80% sequence identity to any one of SEQ ID NOs: 1-25; a second complementarity determining region comprising a polypeptide sequence having at least 80% sequence identity to any one of SEQ ID NOs: 26-50; and a third complementarity determining region comprising a polypeptide sequence having at least 80% sequence identity to any one of SEQ ID NOs: 51-75.

The binding domain can also be characterized by its binding affinity to a binding sequence. The terms "binding sequence," "binding domain," or "binding site", as used herein, refer to the portion, region, or site of polypeptide that mediates specific binding with a target molecule (e.g., a brain cell or a cell resident in the brain). Exemplary binding domains include an antigen binding site (e.g., a VHH or VH domain) or molecules comprising such a binding site (e.g., an antibody or a single domain antibody). A plurality of CDRs together form a binding domain for the sdAb construct, such as CDR1, CDR2, and CDR3.

In an embodiment, within the variable domain of the sdAb construct, three CDRs can be present. The CDRs can include a first CDR, a second CDR, and a third CDR. Any of these CDRs can be a polypeptide sequence having at least 80% sequence identity to any of SEQ ID NOs: 1-75. A fragment can be covered by the at least 80% sequence identity, for example, including a polypeptide that is one, two, or three amino acids shorter than the reference sequence of any of SEQ ID NOs: 1-75. The omitted amino acid(s) can be removed from the C-terminus and/or the N-terminus. Omitted amino acid(s) can also be included under the sequence identity percentage. In an embodiment, the sdAb construct is different in the first and second binding regions, and the first and second binding regions are different from each other and each binding region binds to a different epitope on a target disclosed herein.

The sdAbs can be arranged in a structure including the CDRs disclosed herein, and corresponding to the structure disclosed in FIG. 4. Such sdAb sequences include framework regions FR1, FR2, FR3, and FR4, and CDR1, CDR2, and CDR3. In an embodiment, a sdAb construct comprises CDRs and framework regions (FRs). As can be seen, each CDR can be disposed between two FRs. An exemplary construct can include framework region 1 (FR1) attached to an N-terminus of CDR1; FR2 disposed between CDR1 and CD2; FR3 disposed between CDR2 and CDR3; and FR4 attached to a C-terminus of CDR3. Examples of sequences for CDR1, CDR2, and CDR3 include, e.g., any sequences for first CDR, second CDR, and third CDR, respectively, as described herein.

In an embodiment, the targeting or any other sdAbs of the sdAb construct have a structure corresponding to FIG. 4 and comprises a polypeptide sequence having at least 90% sequence identity (such as at least 95% or at least 98%) to any one of SEQ ID NOs: 76-100 (FIG. 5 and FIG. 6). In another embodiment, the FR regions of the sdAb can be selected from those disclosed below, but the CDR regions are selected from those in any one of SEQ ID NOs: 1-75 (FIG. 3) and in the same order of CDR1, CDR2, and CDR3. Such sdAbs have usefulness as targeting brain tissue and have shown greater selectivity to the brain over other organs.

In an embodiment, the sdAbs are part of a sdAb construct comprising: a first and second sdAb and an Fc domain and hinge region of human IgG1 protein. The first and second sdAbs comprise a first framework region coupled to a first complementarity determining region, a second framework region coupled to the first complementarity determining region and a second complementarity determining region, a third framework region coupled to the second complementarity determining region and a third complementarity determining region, and a fourth framework region coupled to the third complementarity determining region. The first complementarity determining region comprises a polypeptide sequence having at least 80% sequence identity (such as at least 85% or at least 90%) to any one of SEQ ID NOs: 1-25; the second complementarity determining region comprising a polypeptide sequence having at least 80% sequence identity (such as at least 85% or at least 90%) to any one of SEQ ID NOs: 26-50; and the third complementarity determining region comprising a polypeptide sequence having at least 80% sequence identity (such as at least 85% or at least 90%) to any one of SEQ ID NOs: 51-75. The sdAb is coupled to the hinge region of the Fc domain.

Figure 7:
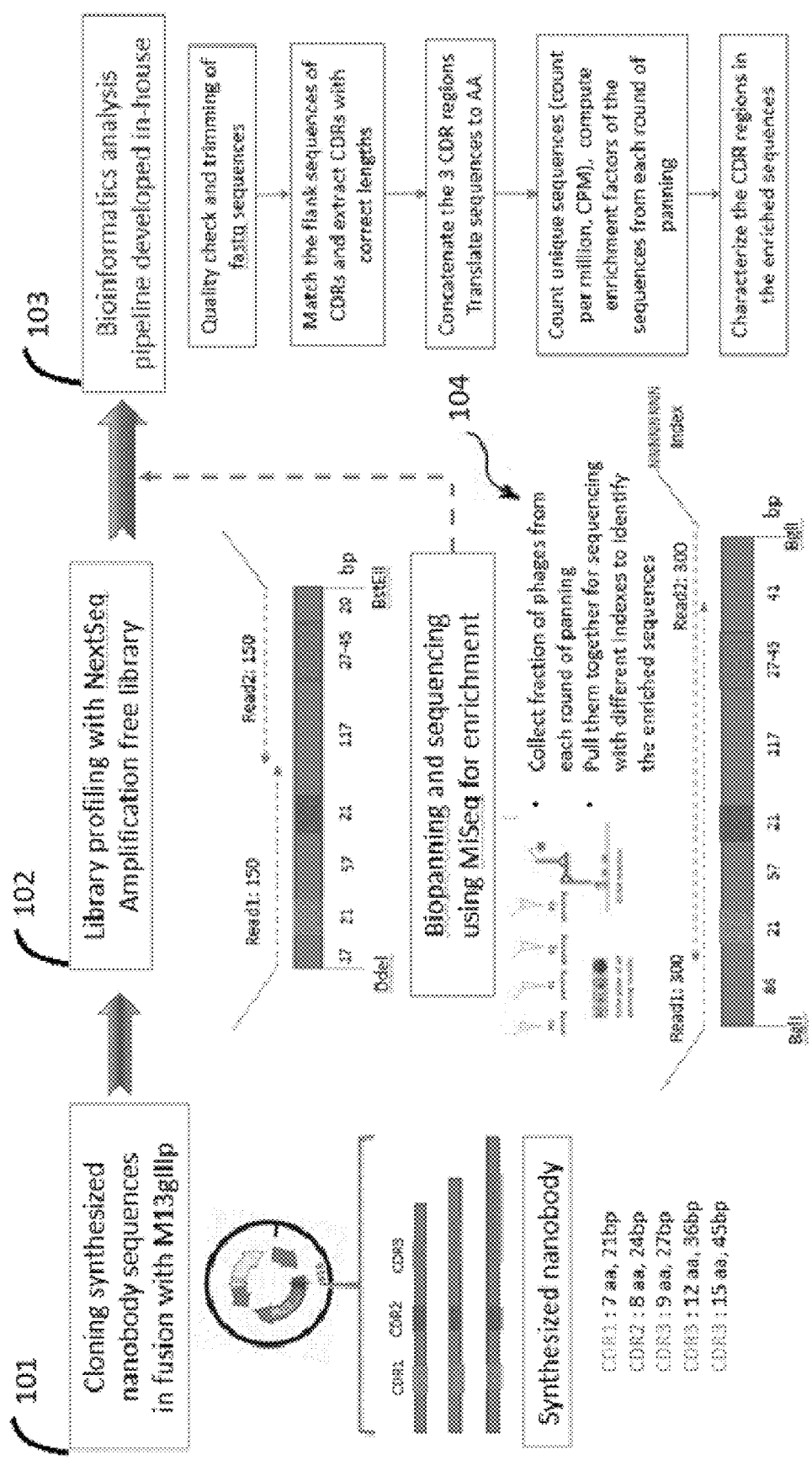
FIG. 7 is general schematic of exemplary library cloning, in vivo biopanning technique, and the bioinformatics analysis as disclosed herein.

FIG. 7 lists sequences for framework regions FR1, FR2, FR3, and FR4 (SEQ ID NOs. 310-313, respectively), which are disposed adjacent and/or between the regions indicated as CDR1, CDR2, and CDR3 as shown in FIG. 4. These framework regions are utilized in the examples herein.

FIG. 15 lists additional sequences for framework regions FR1, FR2, FR3, and FR4, which are disposed adjacent and/or between regions indicated as CDR1, CDR2, and CDR3 as shown in FIG. 4.

In an embodiment, the sdAb constructs herein include other FRs described herein. FIG. 16A provides non-limiting FR1 sequences. In some embodiments, the first FR includes or is a polypeptide sequence having at least 90% (such as at least 95% or at least 98%) sequence identity to SEQ ID NOs: 190-212.

FIG. 16B provides non-limiting FR2 sequences. In some embodiments, the second FR includes or is a polypeptide sequence having at least 90% (such as at least 95% or at least 98%) sequence identity to SEQ ID NOs: 220-243.

FIG. 16C provides non-limiting FR3 sequences. In some embodiments, the third FR includes or is a polypeptide sequence having at least 90% (such as at least 95% or at least 98%) sequence identity to SEQ ID NOs: 250-284.

FIG. 16D provides non-limiting FR4 sequences. In some embodiments, the fourth FR includes or is a polypeptide sequence having at least 90% (such as at least 95% or at least 98%) sequence identity to SEQ ID NOs: 290-301.

The sdAb construct may be expressed by a vector, such as a phage, yeast, mRNA, ribosomes, or a lentivirus. The phage is configured to express the sdAb with the binding domain comprising: a first complementarity determining region comprising a polypeptide sequence having at least 80% sequence identity to any one of SEQ ID NOs: 1-25; a second complementarity determining region comprising a polypeptide sequence having at least 80% sequence identity to any one of SEQ ID NOs: 26-50; and a third complementarity determining region comprising a polypeptide sequence having at least 80% sequence identity to any one of SEQ ID NOs: 51-75.

In an embodiment, the phage is a bacteriophage, such as a phage configured for the E. Coli host, for example, T4, T7, Lambda, Fd, M3, M7, or M13 bacteriophage.

The sdAbs disclosed herein can target cells such as endothelial cells contributing to the BBB of the mammalian or human brain, including the cell surface receptors contributing to RMT across the BBB.

The sdAb constructs with the sdAb shuttles disclosed herein are capable of passing the blood brain barrier, a network of microvascular endothelial cells lining the cerebral capillaries that penetrate the brain and spinal cord. The sdAb constructs may also pass the blood-cerebrospinal fluid barrier, formed by the epithelial cells of the choroid plexus. Finally, the sdAb constructs may also pass the avascular arachnoid epithelium. The small size of the sdAb constructs contribute to this ability and small cargo sizes (such as other sdAbs) may be desirable to pair with the sdAb shuttles disclosed herein.

A secondary target as disclosed herein is a target of the cargo of the sdAb construct, which can be an active biochemical species, such as another sdAb, or a pharmaceutical. The secondary target can be an antigen that can be bound by a sdAb construct described herein. Non-limiting targets include a virus, e.g., an alphavirus, a malignancy, such as cancer, ailments of the central nervous system, or a bacterial infection. Plaques associated with Alzheimer's disease e.g., amyloid plaques, and the beta-amyloid protein may be a secondary target.

Non-limiting portions of a coronavirus that may be a secondary target include SARS-CoV-2, includes a spike protein (e.g., a S-glycoprotein) or a receptor-binding domain (RBD).

The present disclosure encompasses a sdAb construct that can be directly or indirectly attached (i.e., coupled) to one or more therapeutic or diagnostic agents (cargo). Such agents can include a therapeutic antibody, a complementarity determining region (CDR) (e.g., from another sdAb), a small molecule drug, a chemotherapeutic agent, an antiviral agent, an antibacterial agent, an anti-inflammatory agent, a scavenging agent, an imaging agent, a marker, a dye, a detectable moiety, or a label.

Small size and water solubility of the sdAb construct are advantageous without additional attachments to promote delivery to the body, targeting brain tissue, and circulation within the body. The sdAb attached to a humanized Fc still provides solubility and targeting benefits, but also promotes signaling the body's own immune response and keeping the sdAb circulating in the blood stream without being filtered out by the kidneys.

Any of the constructs herein (e.g., sdAbs, sdAbs bound to humanized Fc) can be employed to bind to a target. Binding can be accomplished, e.g., by using CDRs specific for that target, such as those disclosed herein. In one embodiment, the construct includes one or more CDRs for viral targets. Exemplary targets include a virus, such as Coronaviridae (e.g., severe acute respiratory syndrome-related coronavirus (SARS-COV), severe acute respiratory syndrome coronavirus 2 (SARS-COV-2), or variants thereof); or a portion of a virus, such as a spike protein or a receptor-binding domain (RBD) of a coronavirus. It should be noted that SARS-COV-2 has been reported to pass the blood brain barrier. Zhang, L., Zhou, L., Bao, L. et al. "SARS-COV-2 crosses the blood-brain barrier accompanied with basement membrane disruption without tight junctions alteration," *Sig Transduct Target Ther* 6, 337 (2021).

Other non-limiting therapeutic or diagnostic agents include a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; or a lipopolysaccharide.

Non-limiting detectable moieties for diagnostic agents may be a radioisotope (e.g., $^{32}P$), a fluorescent or chemiluminescent compound such as rhodamine or luciferin, or an enzyme, such as alkaline phosphatase or horseradish peroxidase. Non-limiting labels include a radiolabel, an isotope, a visible or near-infrared fluorescent label, a reporter molecule, or biotin.

The therapeutic or diagnostic agent can be a peptide, an enzyme (e.g., horseradish peroxidase, alkaline phosphatase, glucose-6-phosphatase or Beta-galactosidase), a nucleic acid, a virus, a fluorophore (e.g., green fluorescent protein (GFP), blue fluorescent dyes excited at wavelengths in the ultraviolet (UV) part of the spectrum (e.g., AMCA (7-amino-4-methylcoumarin-3-acetic acid); ALEXA FLUOR 350), green fluorescent dyes excited by blue light (e.g., FITC, Cy2, ALEXA FLUOR 488), red fluorescent dyes excited by green light (e.g., rhodamines, TEXAS RED, Cy3, ALEXA FLUOR dyes 546, 564 and 594), or dyes excited with far-red light (e.g., Cy5) to be visualized with electronic detectors (CCD cameras, photomultipliers)), a heavy metal (including chelates thereof, such as those including europium, lanthanum or yttrium), a chemical entity, or a radioisotope (e.g., [$^{18}$F]fluorodeoxy glucose, $^{11}$C—, $^{125}$I—, $^{131}$I—, $^{3}$H—, $^{14}$C—, $^{35}$S—, or $^{99}$Tc-labelled compounds).

The therapeutic or diagnostic agent can include a drug, an antigen binding fragment of an antibody molecule or portion thereof (e.g., F(ab), scFv, a VH domain, or a VL domain) (e.g., to impart, induce or block a biological response), a ligand binding portion of a receptor or a receptor binding portion of a ligand, an enzyme, therapeutically useful amino acids, peptides, proteins, nucleic acids, including but not limited to polynucleotides, oligonucleotides, carbohydrates and lipids. Yet other exemplary agents include cytokines, neurotrophic factors, growth factors, enzymes, antibodies, neurotransmitters, neuromodulators, antibiotics, antiviral agents, antifungal agents, imaging or detectable agents, isotopes, and chemotherapeutic agents, and the like. The therapeutic or diagnostic agents can also include drugs, prodrugs, and precursors that can be activated when the therapeutic agent is delivered to the target tissue.

The present disclosure also encompasses methods that employ any construct described herein. In particular embodiments, the methods include methods of treatment, diagnosis or prophylaxis of one or more diseases or conditions.

Methods can also include use of the construct as a therapeutic or diagnostic agent, which can be administered to a subject (a mammal or a human) by inhalation, oral, nasal, injection, intravenous, intraperitoneal, intramuscular or subcutaneous injection. The constructs herein (e.g., with a therapeutic or diagnostic agent) can be used in imaging or in diagnosing viral spread.

Methods can also include providing a construct or a pharmaceutical composition thereof (e.g., as described herein) for use in the treatment of viral infections or any disease, malignancy, or condition herein. A pharmaceutical composition can include any construct, described herein either with a therapeutic or diagnostic agent, and a pharmaceutically acceptable carrier.

As used herein, "pharmaceutically acceptable carrier" is intended to include pharmaceutically acceptable salts, adjuvants, dispersion media, coatings, antibacterial and antifungal agents, isotonic and absorption delaying agents, and the like, compatible with pharmaceutical administration. Pharmaceutically acceptable salts include the acid addition salts (formed with the free amino groups of the polypeptide or antibody molecule) which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Suitable carriers include those disclosed in the most recent edition of *Remington's Pharmaceutical Sciences*, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

Nanoparticles such as those disclosed in U.S. 2019/0091150 may be part of the sdAb construct, wherein the shuttle sdAb is a cargo on the nanoparticle and another cargo is associated with the same construct.

For performing the in vivo biopanning methods were developed for concentrating and purifying the phage library so that living organisms could better process the phage/sdAbs. To this end, an isoelectric precipitation and endotoxin removal step were employed.

In an embodiment, lysate of the phagemid cells comprising DNA inserts of a sequence configured to allow for expression of the sdAb, e.g., the sdAbs disclosed herein are mixed with an acid, such as a strong acid, e.g., HCl. (See FIG. 8, 202.) The addition of acid may reduce the pH of the solution by 1 to 3 pH, such as 1.25 to 2.5, or 1.5 to 2 pH. In an embodiment, the initial pH of the solution is 5 to 7 pH, such as, 5.5 to 6.5 or about 6.0.

This causes an isoelectric precipitation in the solution, resulting in a precipitate of the lysate. Precipitation can be encouraged by gravimetric means, such as centrifugation.

After isolation of the precipitate, it can be resuspended and precipitated multiple times with a polar liquid, e.g., sterilized water. After 1 to 5, e.g., 2 to 3 resuspension steps, the suspended product in polar liquid can be stored with refrigeration and pH can be adjusted to 6.5 to 7.5 pH, or approximately neutral.

In an endotoxin removal step, a nonionic surfactant, such as Triton-X-114 (a secondary alcohol ethoxylate, nonionic surfactant) is added to neutralize endotoxins in the purified phage lysate sample. The resulting mixture can be mixed, e.g., vortexed. Optionally, the process can be accelerated by alternately cooling and heating. For example, cooling can be with an ice bath or freezer, at just above freezing (near 32° F.) to 45° F., e.g., 33° F. to 40° F. for cooling such as with an ice bath. Heating, for example, can be performed in a heat block set at, e.g., 30° C. to 50° C., such as, e.g., 35 to 40° C., or about 37° C. Heating and cooling intervals may be, for example, be 2 to 15 minutes, such as 3 to 10 minutes, or about 5 minutes each. An amount of 1% endotoxin removal agent can be used. In an embodiment, 0.1 to 5% endotoxin removal agent may be used, such as, e.g., 0.5% to 1.5%, or 0.75% to 1.25%.

The suspension should look cloudy when finished. The cloudy suspension can then be separated, for example, with gravimetric means, such as centrifuging, and at elevated temperature, such as 30° C. to 50° C., such as, e.g., 35 to 40° C., or about 37° C. Separation should produce a supernatant at the top of the tube and an oily residue at the bottom at the tube. The final product is the purified and concentrated phage encoding the sdAb from the library.

In pharmaceutical or diagnostic preparations, the final product would be the sdAb construct, including the shuttle sdAb and a cargo. This would be exclusive of phage or other vectors.

EXAMPLES

Example 1: SdAb Development and Library

A high-diversity synthetic sdAb phage library was used to identify humanized sdAbs that show affinity to brain tissue. In particular, a high diversity humanized sdAb library (more than $3\times10^{10}$ sdAb variants) was developed and designed to have three different CDR3 lengths and incorporated the natural prevalence of amino acids at specific CDR positions for CDR1 and CDR2 derived from numerous effective sdAbs. For CDR3, all amino acids were used with the exception of cysteine and methionine. The sequence used for the framework to house the custom made CDRs, hs2dAb, was derived from Moutel et al. In this framework, multiple residues are changed such that the framework more closely mirrors germline human VH3 immunoglobin. To obtain sufficient diversity coverage for the library (i.e., transformants), 150 electroporations were performed yielding approximately $3.38\times10^{10}$ transformants. To determine the level of success for the ligation of the library into the vector backbone, colony PCR was performed. Of the 408 colonies selected, 395 contained the correct size amplified DNA fragment (95.9%). This value was used to adjust the calculated value for library diversity to $3.24\times10^{10}$. Finally, library diversity, quality, and the distribution of CDR3 lengths were assessed by NGS from a total of 39,870,360 reads. The 9-amino acid CDR3 was the most prevalent at 40%, followed by 12-amino acid CDR3 at 34%, and lastly the 15-amino acid CDR3 at 25% of the observed diversity. Overall, there was good coverage of all represented CDR3s. Approximately 1% of sequences contained a stop codon and 99% of reads were unique sequences (38,592,027 reads). Roughly 1% of reads were duplicates, and 0.01%(1,095 sequences) were present in triplicate. With these corrections the adjusted diversity for this sdAb library is $3.18\times10^{10}$.

FIG. 1 generally discloses a method of constructing a sdAb phage library. In particular, the library was constructed using novel DNA synthesis technology, thereby ensuring high quality and full length sdAbs with low incidence of stop codons. These attributes allowed for the identification of highly potent binders to desired targets with femtomolar to nanomolar dissociation constants.

Example 2

FIG. 7 shows an overview of the process by which the sdAbs from the library were sequenced and enriched for determination of interaction with the brain tissue.

At 101, library was developed by cloning into the pADL20c M13 phagemid vector, which allows for expression of sdAbs as a fusion protein to coat protein gIIIp of M13 phage. To display sdAb on M13 phage, the phagemids were constructed with pADL20c as backbone template and with synthesized DNA inserts of the sdAb sequences which were designed by incorporating the natural prevalence of amino acids at positions in CDR1, CDR2 and highly diversified CDR3 with 3 different lengths (9-, 12-, and 15-amino acids).

At 102, library profiling and enriched sequence analysis was performed. Next generation sequencing was performed to evaluate the diversity of the phage library and identify the enriched sequences enrichment from the rounds of biopanning. (See Example 3.) The minimum region containing all 3 CDR domains, approximately 300 bps, was excised by two-step restriction digests, BgII followed by DdeI/BstEII double digests on the gel-purified small fragment from the BgII restriction reaction to cover the entire length of CDR sequences. The sequencing library was prepared with unique indexes for each sample and sequenced on Illumina NextSeq 500/550 platform with High Output v2.5 300-cycles, paired-end mode.

At 103, bioinformatic analysis of the library was performed. Raw sequencing files of the library were converted to FASTQ and demultiplexed by the index sequences. The sequences were processed with quality filtering (Q>=30) and adaptor trimming using fastp with the following parameters, -q 30-l 100-x 7. The processed sequences were reformatted to be reverse complemented and merged with R1 Read using BBTools (BBMap). Sequences were aligned by conserved region and variable regions extracted. Three CDR domains with correct sequence lengths were extracted, concatenated and translated using a custom python script. The normalized abundance was calculated per million sequences for each round of panning and enriched sequence analysis was performed using a custom R script. Sequence counts that are 5 and less were removed and normalized by total reads of each sample per million. The sequences were further filtered by one and above in the enrichment factor, normalized counts of the third round (R3) divided by normalized count of the second round (R2) panning. The CDR3 sequences were clustered to find common motifs.

Example 3

The following steps were taken to scale up the sdAb library and purify it for use in in vivo bio-panning. First, three reagents were made for the steps discussed below.
1. SMPB
   5.8 g of NaCl, 2 g of MgSO4, 50 mL of 1M Tris-HCl (pH 7.5) were mixed, and the volume was brough to 1 L and put in an autoclave set at 121° C. for 20 minutes.
2. LB TA (Lysogeny broth top agar).
   25 g of LB broth, 5 g of agar were mixed in 1 L of $H_2O$. Then the mixture was put in an autoclave.
3. 2.5 M NaCl/20% PEG-8000
   100 g PEG-8000 (20% w/v) and 75 g NaCl (2.5M) were dissolved in 400 mL $H_2O$ and brought to final volume of 500 mL. This was filtered and sterilized.

Phage Spot Titer

100 μL of TG1 *E. Coli* bacteria were mixed with 3 mL of LB TA (as described above) in a 14 mL tube and pipetted onto an LB agar plate (1 plate per titer). These were allowed to dry for about 10-20 minutes. A 10-fold serial dilution of phage was performed (for CM13 dilution out to 10-10) in SMPB (formula for SMPB is described above). CM13 is an interference resistant helper phage engineered for phage display and is available from Antibody Design Labs of San Diego, CA.

3 μL of each dilution were spotted onto the plate and allowed to dry about 20 minutes, then incubated, agar side down, at 37C overnight.

The next day results were viewed and one or more spots had individual plaques. The individual plaques were counted. Titer calculation: titer=pfu/μL spotted*1000*dilution factor.

Phage Full Plate Titer

100 μL aliquots of TG1 were added into 14 mL tubes for each dilution planned for plating. A 10-fold serial dilution of phage was conducted in SMPB.

Then each tube of TG1 was infected with 100 µL of an appropriate dilution of phage and swirled. (CM13 was diluted to 10-6 to 10-10). Infection was performed for 15 minutes at room temperature (e.g., 72° C.). Then 3 mL of LB TA were added to mix the bacteria/phage infection and then plated onto LB agar. The plates were allowed to dry for about 20 minutes, incubate agar side up overnight at 37° C.

Plaques on all plates were counted and titer was calculated as above.

Plate Lysates

A web plate was taken from a previous full plate titer. 8 mL of SMPB were added and this was allowed to sit for 4 hours at room temperature, then overnight at 4° C. The liquid was removed with a syringe, and filtered with a 0.2 µM filter.

Liquid Growth of CM13

20 mL of 2x YT media (available from Sigma Aldrich) were added to 200 µL of TG1 E. coli bacteria (overnight) and 1 µl of CM13 (titer>$10^{10}$). The mixture was shaken at 37° C. for 4 hours. This was then spun at 4500×g for 10 minutes.

Large Scale Phage Precipitation 16 mL of supernatant were transferred to a new tube and 4 mL of 2.5 M NaCl/20% PEG-8000 (w/v) were added and mixed briefly. Phage was allowed to precipitated for 1 hr to overnight (e.g., 11 to 16 hours) at 4° C. (1 hr, 4 hr, and overnight were all performed with good results). This can be done at other volumes with a ratio of about 4:1 lysate to PEG, e.g., 2:1 to 8:1, or 3:1 to 5:1.

Phage was pelleted by centrifugation at 12000×g for 15 min. Supernatant was decanted and the pellet was resuspend in 1 mL TBS and transferred to an Eppendorf tube. The tube was spun for 30 seconds at max speed. Then the supernatant was removed to a new tube and titered. (See FIG. 8, 201.)

Isoelectric Precipitation 5 mL of CM13 lysate was swirled to mix with 29 µL of 6N HCl. (See FIG. 8, 202.) The initial pH was about 6.0 and between 4.0 and 4.5 after HCl addition using pH strips.

The mixture was spun at 10,000×g for 10 min at 20° C. The supernatant was removed with a serological pipette (decanting is also an option). A white pellet was visible along the side of the 50 ml conical tube.

1 mL of filter-sterilized milli-Q water was added and the pellet was vortexed for 1 minute to resuspend it, and spin at 10,000×g for 10 min at 20° C.

Again, the supernatant was removed and the pellet resuspended in 500 µL filter-sterilized milli-Q water. The pH was adjusted to about 7.0 with 1 µL of 10N NaOH and stored at 4° C.

Endotoxin Removal

5 µL of Triton-X-114 (a secondary alcohol ethoxylate, nonionic surfactant) was added to 500 µL of phage lysate from the isoelectric precipitation above. This was mixed in a tube (vortexed) for 20 seconds. (See FIG. 8, 203.)

The tube was placed in an ice bath for 5 minutes and vortexed for 5 seconds every minute for the 5 minutes. The tube was then placed in a heat block set at 37° C. for 5 minutes. The solution was very cloudy when finished. The cloudy solution was then spun at 37° C. 20,000×g for 30 seconds. (There was an oily droplet at the bottom at the tube.)

6.400 µL were removed from the top of the tube being very careful to not disturb the oily droplet. This final product was the purified and concentrated sdAb encoding phage from the library.

The table of FIG. 9 shows the titers of the CM13 phage at the various stages shown in FIG. 8 and the original library stock as received from the lab. The phage was concentrated and purified with a final product titer of 1×$10^{14}$.

Example 4

Figure 12:
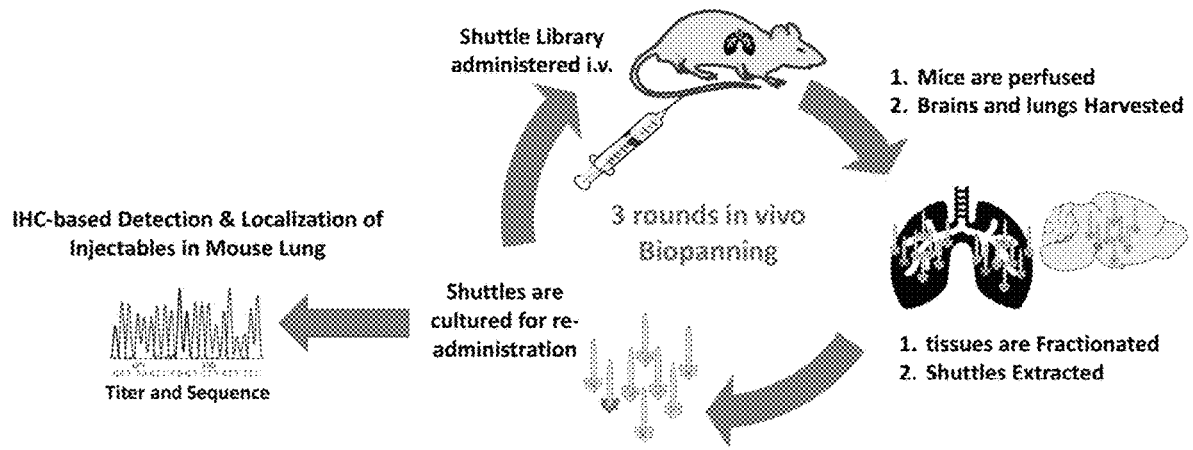
FIG. 12 is a schematic showing the in vivo biopanning technique used in the Examples herein.

The purified final product of Example 3 was then used for in vivo bio-panning in mice (See FIG. 7, step 104, FIG. 8, step 204, and FIG. 12). FIG. 12 shows the general process of the in vivo biopanning wherein the sdAb constructs are described as shuttles. The purified and concentrated library was intravenously injected into 5 mice. The mice brains were harvested one-hour later. The brains were dissociated, and the phage was extracted, grown up, and re-purified. The reprocessed phages from the brains were re-injected into 5 new mice two additional times (harvested and reprocessed as described above) to ensure brain-targeting sdAb enrichment in the brain above other tissues.

FIG. 10 shows data of phage populations at each round of in vivo biopanning and shows the input and output CFUs for each round. The output sample was sequenced to gauge enrichment and selection over time. The experiment was successful in delivering a large library of phage to a mammal in vivo. Through multiple rounds, major down-selection of clones $10^{10}$ to $10^{4}$ was achieved. Also, progressive enrichment over rounds of specific clones was achieved.

From this in vivo biopanning campaign 25 top candidate sdAbs for brain-targeting were identified. These correspond to SEQ ID NOs: 76-100.

FIG. 11 is a table showing the functional enrichment of the top 25 sequences in Round 2 and Round 3 biopanning in terms of enrichment factor.

By the end of the third round of biopanning 13905 sdAbs (11218 of which were unique) found in the brain had been reduced down to a total of 700 (691 of which were unique). Furthermore, the final sequences had been enriched 10 fold or higher.

Example 5

After each round of biopanning the mice were anesthetized using isoflurane. Transcardial perfusion with cold, heparinized saline was performed by inserting a butterfly needle into the left ventricle and clipping a lobe of the liver for drainage; perfusion media was conducted using a peristaltic pump. The organs were harvested and kept on ice for tissue-based ELISA.

Figure 13:
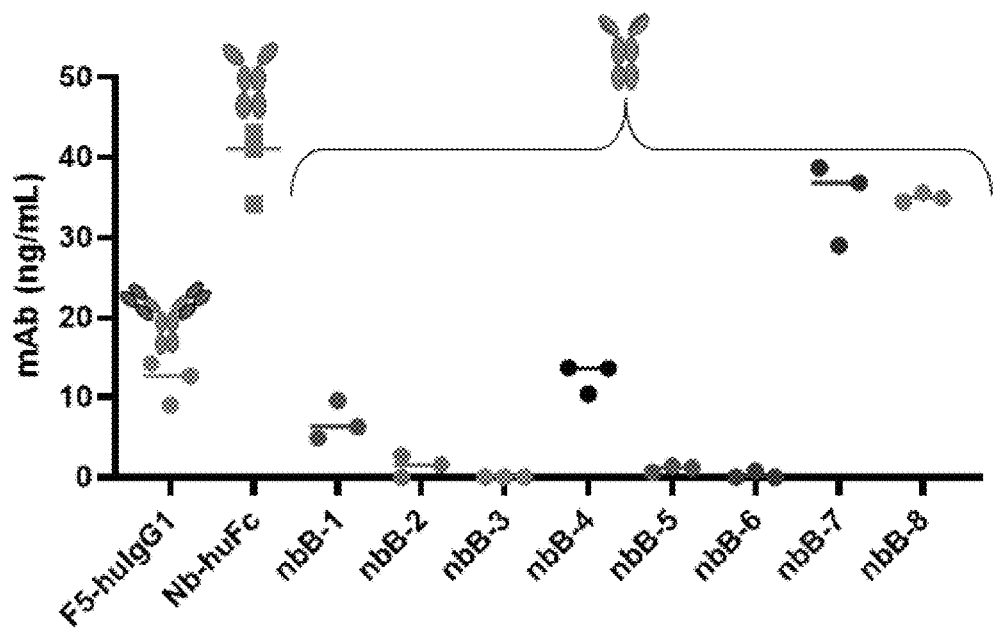
FIG. 13 shows Anti-Human IgG Tissue ELISA analysis of the brain tissue from the mice after three rounds of biopanning.

FIG. 13 shows Anti-Human IgG Tissue ELISA analysis of the brain tissue from the mice after three rounds of biopanning. After biopanning, brain penetration of top sdAbs was tested in the heavy chain only format (NbFc). SdAb constructs were administered IV at a doseage of 100 ug, and at 18 hours post injection, mice were perfused, and brains were harvested. Capillaries were depleted by dextran centrifugation. Anti-human IgG ELISA was used to determine the concentration of antibody or sdAb construct in the brain tissue compared with a non-targeting antibody (F5-huIgG1) and a previously characterized BBB penetrating sdAb (Nb-huFc).

All publications, patents, and patent applications mentioned in this specification are incorporated herein by reference to the same extent as if each independent publication or patent application was specifically and individually indicated to be incorporated by reference.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

The invention claimed is:

1. A single domain antibody construct, comprising a first single domain antibody with a binding domain, wherein the binding domain comprises:
a first polypeptide comprising first, second, and third complementarity determining regions selected from the group consisting of the following combinations:
SEQ ID NOs: 1, 26, and 51, respectively;
SEQ ID NOs: 2, 27, and 52, respectively;
SEQ ID NOs: 3, 28, and 53, respectively;
SEQ ID NOs: 4, 29, and 54, respectively;
SEQ ID NOs: 5, 30, and 55, respectively;
SEQ ID NOs: 6, 31, and 56, respectively;
SEQ ID NOs: 7, 32, and 57, respectively;
SEQ ID NOs: 8, 33, and 58, respectively;
SEQ ID NOs: 9, 34, and 59, respectively;
SEQ ID NOs: 10, 35, and 60, respectively;
SEQ ID NOs: 11, 36, and 61, respectively;
SEQ ID NOs: 12, 37, and 62, respectively;
SEQ ID NOs: 13, 38, and 63, respectively;
SEQ ID NOs: 14, 39, and 64, respectively;
SEQ ID NOs: 15, 40, and 65, respectively;
SEQ ID NOs: 16, 41, and 66, respectively;
SEQ ID NOs: 17, 42, and 67, respectively;
SEQ ID NOs: 18, 43, and 68, respectively;
SEQ ID NOs: 19, 44, and 69, respectively;
SEQ ID NOs: 20, 45, and 70, respectively;
SEQ ID NOs: 21, 46, and 71, respectively;
SEQ ID NOs: 22, 47, and 72, respectively;
SEQ ID NOs: 23, 48, and 73, respectively;
SEQ ID NOs: 24, 49, and 74, respectively; and
SEQ ID NOs: 25, 50, and 75, respectively.

2. The single domain antibody construct of claim 1, further comprising one or more therapeutic or diagnostic agents.

3. The single domain antibody construct of claim 1, further comprising a therapeutic agent selected from the group consisting of: a therapeutic antibody, a small molecule drug, a chemotherapeutic agent, an antiviral agent, an antibacterial agent, an anti-inflammatory agent, and a scavenging agent.

4. The single domain antibody construct of claim 1, further comprising a diagnostic agent selected from the group consisting of: an imaging agent, a marker, a dye, a detectable moiety, and a label.

5. The single domain antibody construct of claim 1, further comprising a second single domain antibody with a second binding domain, wherein the binding domain is configured to target brain cells; and the second binding domain is configured to treat or diagnose a disease or malignancy.

6. The single domain antibody construct of claim 1, further comprising a therapeutic agent with antiviral activity against a coronavirus.

7. The single domain antibody construct of claim 1, wherein the single domain antibody further comprises:
a first framework region attached to an N-terminus of the first complementarity determining region;
a second framework region disposed between the first and second complementarity determining regions;
a third framework region disposed between the second and third complementarity determining regions; and
a fourth framework region attached to a C-terminus of the third complementarity determining region.

8. The single domain antibody construct of claim 1, wherein the first single domain antibody comprises a polypeptide sequence corresponding to any one of SEQ ID NOs: 183-186, wherein CDR1 comprises the first complementarity determining region, wherein CDR2 comprises the second complementarity determining region, and wherein CDR3 comprises the third complementarity determining region.

9. The single domain antibody construct of claim 1, wherein the first single domain antibody is a polypeptide sequence corresponding to any one of SEQ ID NOs: 76-100.

10. The single domain antibody construct of claim 1, wherein the binding domain is configured to penetrate the blood brain barrier and accumulate in the brain tissue.

11. The single domain antibody construct of claim 1, wherein the binding domain is configured to bind to an endothelial cell.

12. The single domain antibody construct of claim 1, wherein the first single domain antibody is expressed as a fusion protein to coat protein gIIIp of M13 phage.

13. A vector comprising:
a phage configured to express a first single domain antibody with a binding domain, wherein the binding domain comprises:
a first polypeptide comprising first, second, and third complementarity determining regions selected from the group consisting of the following combinations:
SEQ ID NOs: 1, 26, and 51, respectively;
SEQ ID NOs: 2, 27, and 52, respectively;
SEQ ID NOs: 3, 28, and 53, respectively;
SEQ ID NOs: 4, 29, and 54, respectively;
SEQ ID NOs: 5, 30, and 55, respectively;
SEQ ID NOs: 6, 31, and 56, respectively;
SEQ ID NOs: 7, 32, and 57, respectively;
SEQ ID NOs: 8, 33, and 58, respectively;
SEQ ID NOs: 9, 34, and 59, respectively;
SEQ ID NOs: 10, 35, and 60, respectively;
SEQ ID NOs: 11, 36, and 61, respectively;
SEQ ID NOs: 12, 37, and 62, respectively;
SEQ ID NOs: 13, 38, and 63, respectively;
SEQ ID NOs: 14, 39, and 64, respectively;
SEQ ID NOs: 15, 40, and 65, respectively;
SEQ ID NOs: 16, 41, and 66, respectively;
SEQ ID NOs: 17, 42, and 67, respectively;
SEQ ID NOs: 18, 43, and 68, respectively;
SEQ ID NOs: 19, 44, and 69, respectively;
SEQ ID NOs: 20, 45, and 70, respectively;
SEQ ID NOs: 21, 46, and 71, respectively;
SEQ ID NOs: 22, 47, and 72, respectively;
SEQ ID NOs: 23, 48, and 73, respectively;
SEQ ID NOs: 24, 49, and 74, respectively; and
SEQ ID NOs: 25, 50, and 75, respectively.

14. The vector of claim 13, wherein the phage comprises an M13 bacteriophage.

15. The vector of claim 13, wherein the first single domain antibody is expressed as a fusion protein to coat protein gIIIp of M13 bacteriophage.

16. The vector of claim 13, wherein the first single domain antibody is a polypeptide sequence corresponding to any one of SEQ ID NOs: 76-100.

17. The vector of claim 13, wherein the binding domain is configured to penetrate a blood brain barrier and accumulate in the brain tissue.

18. The vector of claim 13, wherein the binding domain is configured to bind to an endothelial cell.

19. The single domain antibody construct of claim 1, wherein the first polypeptide comprising first, second, and third complementarity determining regions are selected from the group consisting of the following combinations:
 SEQ ID NOs: 1, 26, and 51, respectively;
 SEQ ID NOs: 2, 27, and 52, respectively;
 SEQ ID NOs: 3, 28, and 53, respectively; and
 SEQ ID NO: 4, 29, and 54, respectively.

\* \* \* \* \*